(12) United States Patent
Giovannini et al.

(10) Patent No.: US 11,155,539 B2
(45) Date of Patent: Oct. 26, 2021

(54) 4-PYRIDINYLMETHYL-MORPHOLINE DERIVATIVES AND THE USE THEREOF AS MEDICAMENT

(71) Applicant: Boehringer Ingelheim International GmbH, Ingelheim am Rhein (DE)

(72) Inventors: Riccardo Giovannini, Biberach an der Riss (DE); Angelo Ceci, Mittelbiberach (DE); Cornelia Dorner-Ciossek, Warthausen (DE); Roland Pfau, Mittelbiberach (DE); Dieter Wiedenmayer, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/654,032

(22) Filed: Oct. 16, 2019

(65) Prior Publication Data
US 2020/0123141 A1  Apr. 23, 2020

(30) Foreign Application Priority Data
Oct. 17, 2018 (EP) .................................. 18 200 987

(51) Int. Cl.
*C07D 413/06* (2006.01)
(52) U.S. Cl.
CPC .................................. *C07D 413/06* (2013.01)
(58) Field of Classification Search
CPC .................................................... C07D 413/06
See application file for complete search history.

(56) References Cited

U.S. PATENT DOCUMENTS

2002/0055519 A1    5/2002  Thompson et al.

FOREIGN PATENT DOCUMENTS

| WO | 2003010159 A1 |   | 2/2003 |
|----|---------------|---|--------|
| WO | 2010088408 A2 |   | 8/2010 |
| WO | 2014060398 A1 |   | 4/2014 |
| WO | 2015130905 A1 |   | 9/2015 |
| WO | WO 2015/130905 | * | 9/2015 |
| WO | 2016029146 |   | 2/2016 |

OTHER PUBLICATIONS

International Search Report and Written Opinion for PCT 2018/083728 dated Feb. 4, 2019.
Murrough, "Antidepressant Efficacy of Ketamine in Treatment-Resistant Major Depression: A Two Site Randomized Controlled Trial", Am. J. Psychiatry, 2013, vol. 170, p. 1134-1142.
Singh, "Intravenous Eskatamine in Adult Treatment-Resistant Depression: A double-Blind, Double-Randomization, Placebo Controlled Study", Society of Biological Psychiatry, vol. 80, 2016, p. 424-431.
Berman, "Antidepressant effects of Ketamine in depressed patients", Biological Psychiatry, vol. 47, 2000, p. 351-354.
Krystal, "Subanesthetic Effects of the Noncompetitive NMDA Antagonist, Ketamine in Humans", Arch. Gen. Psychiatry, 1994, vol. 51, p. 199-214.
Paoletti, NMDA receptor subunit diversity: impact on receptor properties, synaptic plasticity and disease, Nature Reviews, vol. 14, 2013.
Miller, "GluN2B-contaning NMDA receptors regulate depression-like behavior and are critical for the rapid antidepressant actions of ketamine", eLife3e03581, 2014.
Kiselycznyk, "NMDA receptor subunits and associated signaling molecules mediating anti-depressant related effects of NMDA-GluN2B antagonism", Bhav. Nrain Res. 2015, p. 89-95.
Jimemez-Sanchez, "The Role of GluN2A and GluN2B Subunits on the effects of NMDA receptor Antagonists in modeling Schizophrenia and treating Refractory Depression", Neuropsychopharmacology, 2014.
Taylor, "Absolute Oral Bioavailability of Traxoprodil in Cytochrome P450 2D6 Extensive and Poor Metabolisers", Clin. Pharmacokinet, 2006, vol. 45, p. 989-1001.
Addy, "Single dose Administration of MK-0657, an NR2B-Selective NMDA Antagonist", J. of Clinical Pharmacology, 2009, p. 856-864.
Layton, "Discovery of 3-Substituted Aminocyclopentanes as Potent and Orally Bioavailable NR2B Subtype-Selective NMDA Antagonists", ACS Chem. Neuroscience, 2011.
Traynelis, Glutamate Receptor Ion Channels: Structure, Regualtion and Function, Pharmacology reviews, 2010, vol. 62.
Chaffey, NMDA receptor subtypes, Current Anesthesia and Critical Care, 2008, vol. 19, p. 183-201.
Mony, Allosteric modulators of NR-2B-containing NMDA receptors, Bristish Journal of Pharmacology, vol. 157, 2009.
Preskom, An Innovative Design to Establish Proof of Concept of the Antidepressant effects of the NR2B Subunit Selective N-Methyl D-Aspartate Antagonist CP-101, 606, Journal of Clinical Pharmacology, vol. 28, 2008.
Beinat, Insights into Structure related activity relationships, Current Medicinal Chem, 2010. vol. 17, p. 4166-4190.
Serafini, The Role of Ketamine in Treatment resistant Depression, Current Neurapharmacology, 2014, vol. 10, p. 444-461.

\* cited by examiner

*Primary Examiner* — Valerie Rodriguez-Garcia
(74) *Attorney, Agent, or Firm* — David L. Kershner

(57) ABSTRACT

Disclosed are 4-pyridinylmethyl-morpholines of formula A

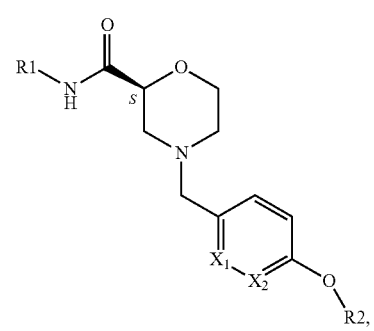

and pharmaceutically acceptable salts thereof, wherein $R^1$ and $R^2$ are defined herein. Also disclosed are processes for their preparation, pharmaceutical compositions containing the compounds, and their use in therapy, particularly in the treatment or prevention of conditions having an association with NR2B negative allosteric modulating properties.

12 Claims, 2 Drawing Sheets

P1 – pulse 1; P25 – pulse 25.

4-PYRIDINYLMETHYL-MORPHOLINE DERIVATIVES AND THE USE THEREOF AS MEDICAMENT

FIELD OF THE INVENTION

The present invention relates to novel 4-pyridinylmethyl-morpholine derivatives processes for their preparation, pharmaceutical compositions containing them and their use in therapy, particularly in the treatment or prevention of conditions having an association with NR2B negative allosteric modulating properties. The compounds of the invention show NR2B negative allosteric modulating properties.

BACKGROUND OF THE INVENTION

Extensive studies over the past twenty years have indicated that N-methyl-D-aspartate receptors (NMDA) play a relevant role in Alzheimer's disease, Parkinson's disease, dyskinesia, stroke, motor neuron disease, psychosis, epilepsy, anxiety, schizophrenia and pain.

The non-selective NMDA receptor antagonist ketamine, (racemic as well as the S enantiomer), a medication mainly used for starting and maintaining anaesthesia, has demonstrated over the last years clinical efficacy in treating major depressive disorder (MDD) at subanaesthetic doses (Murrough et al. 2013, Am J Psychiatry. 170: 1134; Singh et al. 2016, Biol Psychiatry. 80: 424). More precisely, ketamine elicits a rapid onset of efficacy which lasts several days in MDD patients insufficiently responding to standard drug therapy (Berman et al. 2000. Biol Psychiatry 47:351, Serafini et al. 2014. Curr. Neuropharmacol.12:444). However, non-selective NMDA receptor antagonists have a range of undesirable effects which limit their application. In particular dissociative and psychogenic side effects are prominent for the non-selective NMDA receptor antagonists such as ketamine (Krystal et al. 1994. Arch. Gen. Psychiatry 51:199). In the early 1990s, it was found that multiple NMDA receptor subtypes exist, which contain different NR2(A-D) subunits (Paoletti et al., 2013 Nat Rev. Neurosci 14:383). More recently, NR2B subtype selective NMDA receptor negative allosteric modulators (NR2B NAM) have raised interest and have shown potential in a wide range of clinical indications, such as attention, emotion, mood, and pain, as well as being involved in a number of different human disorders (Mony et. al. 2009. Br. J. Pharmacol. 157:1301; Chaffey et al., Current Anaesthesia & Critical Care 19, 183). In particular, NR2B NAM have also demonstrated antidepressant efficacy in the early stage of clinical trials (Preskorn et al. 2008. J Clin Psychopharmacol 70:58). Preclinical studies using NR2B NAM as well as applying various transgenic mice strains have shown that NR2B containing NMDA-receptors are mediating the positive effect of ketamine in e.g. the Forced Swim Test (Miller et al. 2014 eLife 3:e03581; Kiselycznyk et al. 2015, Behav Brain Res, 287:89). Furthermore, selective NR2B NAM have advantages over unselective NMDA receptor antagonists, such as ketamine, due to greatly diminished dissociative and psychotomimetic side effects (Jimenez-Sanchez et al. 2014. Neuropsychopharmacology 39:2673). NR2B NAM described to date have exhibited drawbacks with regard to their receptor pharmacology and/or to other drug properties which have limited potential use in human drug therapy (Taylor, et al., 2006, Clin Pharmacokinet.45: 989; Addy et al. 2009 J of Clinical Pharmacology 49:856)).

WO2015/130905 discloses compounds of formula (I)

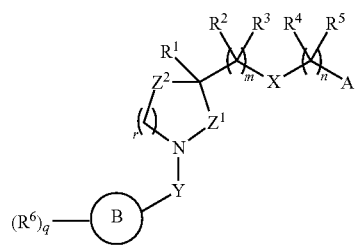

that are inhibitors of Nav1.6 useful in the treatment of multiple sclerosis, polyneuritis, multiple neuritis, amyotrophic lateral sclerosis, Alzheimer's disease or Parkinson's disease. WO2015/130905 discloses the specific examples 100, 105, 106 and 107 in which ring B corresponds to a meta-disubstituted phenyl ring.

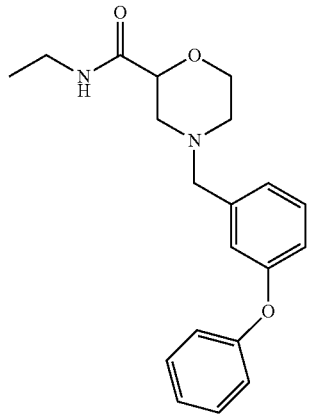

Example 100

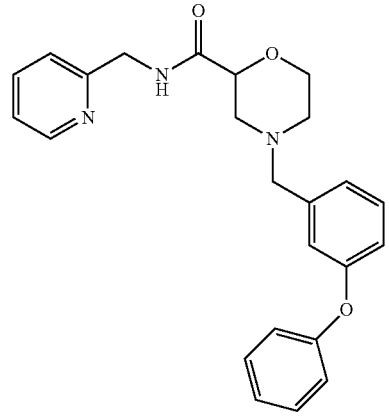

Example 105

WO2015/130905 reports specific examples 100, 105, 106 and 107 to be weak Nav1.6 inhibitors (Nav 1.6 blockage of examples 100, 105 and 107 at 1-5 µM, and Nav 1.6 blockage of example 106 at >5 µM).

SUMMARY OF THE INVENTION

The present invention provides novel 4-Pyridinylmethyl-morpholine derivatives of formula A in which
$X_1$ is N and $X_2$ is CH, or
$X_1$ is CH and $X_2$ is N,
$R^1$ represents methyl, ethyl, propyl, iso-propyl, cyclopropyl, $H_3C-CH_2-CH_2-CH_2-$, cyclobutyl;

$R^2$ represents phenyl which is optionally substituted with 1, 2 or 3 substituents selected from the group consisting of fluoro, chloro, methyl, ethyl, cyclopropyl;
or a salt thereof, particularly a pharmaceutically acceptable salt thereof.

According to another embodiment, the present invention comprises compounds of the general formula A1 or formula A2 in which $R^1$ and $R^2$ have the same meaning as defined in any of the preceding embodiments.

In another embodiment, in the general formula A, A1, A2, $X_1$, $X_2$, $R^2$ have the same meaning as defined in any of the preceding embodiments, and
$R^1$ represents methyl.

In another embodiment, in the general formula A, A1, A2, $X_1$, $X_2$, $R^1$ have the same meaning as defined in any of the preceding embodiments, and
$R^2$ represents -continued

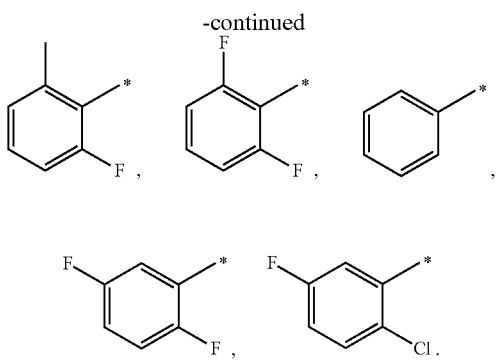

Compounds of the present invention are generically encompassed by formula (I) of WO2015/130905. The compounds of the present invention differ structurally from the examples 100, 105, 106 and 107 explicitly disclosed in WO2015/130905 in that they contain a para-disubstituted pyridyl substructure in place of the meta-disubstituted phenyl ring.

The structural differences unexpectedly result in potent NR2B negative allosteric modulators (see Table 1), whereas the specific examples 100, 105, 106 and 107 of WO2015/130905 do not show any activity on the NR1-NR2B ion channel (see Table 2). Furthermore, compounds of the present invention do not inhibit Nav 1.6 at concentrations at which specific examples 100 and 105 of WO2015/130905 inhibit Nav 1.6 (5 µM; see Tables 3 and 4).

Further, the compounds of the present invention show good membrane permeability and no in vitro efflux (see Table 5 for MDCK assay MDR1 (P-gp)). Therefore, compounds of the present invention are expected to show a favorable brain penetration which is required for efficacious CNS medicaments.

The MDCK assays provide information on the potential of a compound to pass the blood brain barrier. Permeability measurements across polarized, confluent MDCK-MDR1 cell monolayers grown on permeable filter supports are used as an in vitro absorption model: apparent permeability coefficients (PE) of the compounds across the MDCK-MDR1 cell monolayers are measured (pH 7.4, 37° C.) in apical-to-basal (AB) and basal-to-apical (BA) transport direction. The AB permeability (PEAB) represents drug absorption from the blood into the brain and the BA permeability (PEBA) drug efflux from the brain back into the blood via both, passive permeability as well as active transport mechanisms mediated by efflux and uptake transporters that are expressed on the MDCK-MDR1 cells, predominantly by the overexpressed human MDR1. Identical or similar permeabilities in both transport directions indicate passive permeation (PEBA/PEAB≤1), vectorial permeability points to additional active transport mechanisms. Higher PEBA than PEAB (PEBA/PEAB>5) indicates the involvement of active efflux mediated by MDR1, which might compromise the goal to achieve sufficient brain exposure. Therefore, this assay provides valuable support for selection of compounds applicable for further in vivo testing. High permeability not limited by efflux at the blood brain barrier is a favorable characteristic for compounds that are to be used for drugs acting primarily in the CNS.

Further, the compounds of the present invention are metabolically stable in human liver microsomes (see Table 6, metabolic stability). Therefore, compounds of the present invention are expected to have a favorable in vivo clearance and thus the desired duration of action in humans.

Stability in human liver microsomes refers to the susceptibility of compounds to biotransformation in the context of selecting and/or designing drugs with favorable pharmacokinetic properties. The primary site of metabolism for many drugs is the liver. Human liver microsomes contain the cytochrome P450s (CYPs), and thus represent a model system for studying drug metabolism in vitro Enhanced stability in human liver microsomes is associated with several advantages, including increased bioavailability and adequate half-life, which can enable lower and less frequent dosing of patients. Thus, enhanced stability in human liver microsomes is a favorable characteristic for compounds that are to be used for drugs.

Consequently, compounds of the present invention must be more viable for human use.

The objective technical problem is thus to provide potent and selective NR2B negative allosteric modulators.

DETAILED DESCRIPTION OF THE INVENTION

Figure 1:
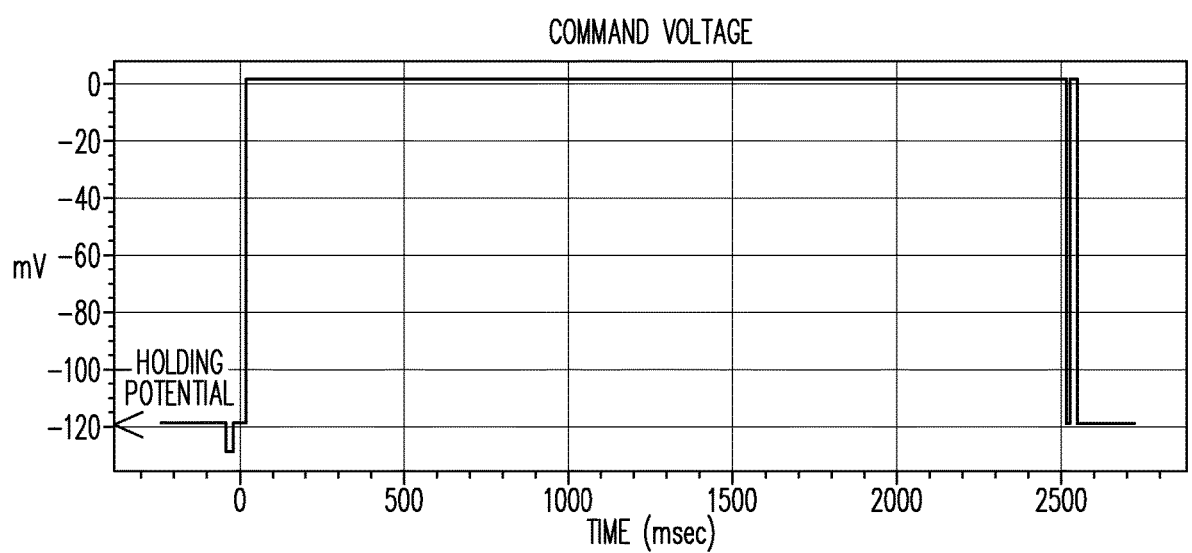
FIG. 1 shows Tetracaine inhibition of Nav1.6.

The present invention provides novel 4-Pyridinylmethylmorpholine derivatives of general formula A that unexpectedly are potent and selective negative allosteric modulators of NR2B.

Another aspect of the invention refers to compounds according to formula A as potent and selective NR2B negative allosteric modulators having high membrane permeability and no in vitro efflux.

Another aspect of the invention refers to compounds according to formula A as potent and selective NR2B negative allosteric modulators having high metabolic stability in human liver microsomes.

Another aspect of the invention refers to compounds according to formula A as potent and selective NR2B negative allosteric modulators having high membrane permeability, no in vitro efflux, and high metabolic stability in human liver microsomes.

Another aspect of the invention refers to pharmaceutical compositions, containing at least one compound according to formula A optionally together with one or more inert carriers and/or diluents.

A further aspect of the present invention refers to compounds according to formula A, for the use in the prevention and/or treatment of disorders associated with NR2B negative allosteric modulators.

Another aspect of the invention refers to processes of manufacture of the compounds of the present invention.

Preparation

The following schemes shall illustrate generally how to manufacture the compounds according to general formula A and the corresponding intermediate compounds by way of example. The abbreviated substituents may be as defined above if not defined otherwise within the context of the schemes.

Scheme 1

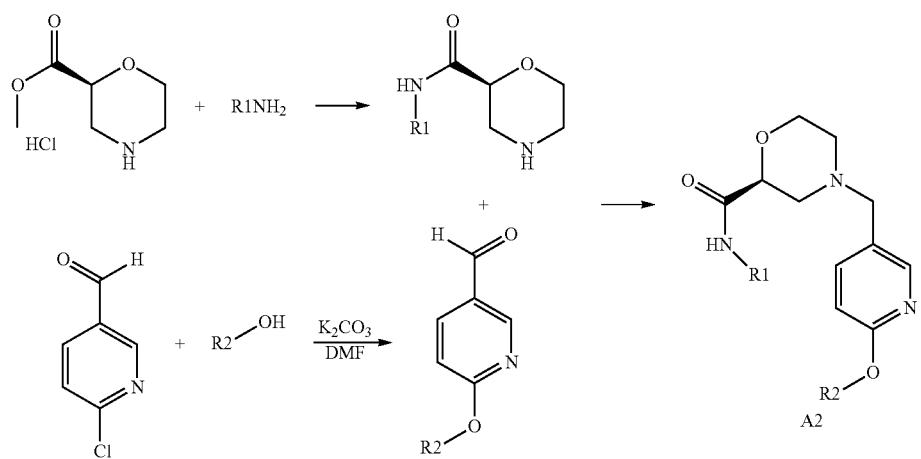

Scheme 1 illustrates the synthesis of pyridine derivatives of general formula A2. The first step is a nucleophilic substitution of a substituted phenol derivative R2-OH and 6-chloro-pyridine-3-carbaldehyde; the last step is represented by a reductive amination involving the aldehyde and a slight excess of an amide derivative of the (S)-Morpholine-2-carboxylic acid obtained by reacting (S)-Morpholine-2-carboxylic acid methyl ester with the corresponding amine R1-NH$_2$.

The described synthetic approach can be used also for gram scale synthesis applying different purification techniques such as crystallization or column chromatography.

The described synthetic approach can be used also for gram scale synthesis applying different purification techniques such as crystallization or column chromatography.

GENERAL DEFINITIONS

Terms not specifically defined herein should be given the meanings that would be given to them by one skilled in the art in light of the disclosure and the context.

NR2B ion channel should be understood as NMDA receptor containing the NR2B protein.

Scheme 2

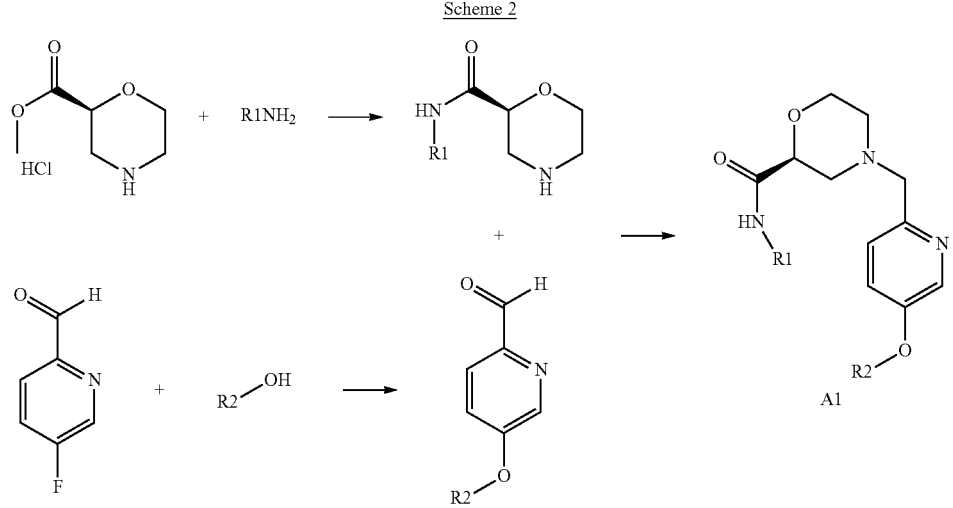

Scheme 2 illustrates the synthesis of pyridine derivatives of general formula A1. The first step is a nucleophilic substitution of a substituted phenol derivative R2-OH and 5-Fluoro-pyridine-2-carbaldehyde; the last step is represented by a reductive amination involving the aldehyde and a slight excess of an amide derivative of the (S)-Morpholine-2-carboxylic acid obtained by reacting (S)-Morpholine-2-carboxylic acid methyl ester with the corresponding amine R1-NH$_2$.

In case a compound of the present invention is depicted in form of a chemical name as well as a formula, the formula shall prevail in case of any discrepancy.

An asterisk may be used in sub-formulas to indicate the bond which is connected to the core molecule or to the substituent to which it is bound as defined.

The term "substituted" as used herein means that any one or more hydrogens on the designated atom is replaced with a selection from the indicated group, provided that the designated atom's viable valence number is not exceeded, and that the substitution results in a stable compound.

Stereochemistry:

Unless specifically indicated, throughout the specification and the appended claims, a given chemical formula or name shall encompass rotamers, tautomers and all stereo, optical and geometrical isomers (e.g. enantiomers, diastereoisomers, E/Z isomers etc.) and racemates thereof, as well as mixtures in different proportions of the separate enantiomers, mixtures of diastereoisomers, or mixtures of any of the foregoing forms where such isomers and enantiomers exist.

Salts:

The phrase "pharmaceutically acceptable" is employed herein to refer to those compounds, materials, compositions, and/or dosage forms which are, within the scope of sound medical judgment, suitable for use in contact with the tissues of human beings without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound forms a salt or a complex with an acid or a base.

Examples for acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid or tartaric acid.

Examples for cations and bases forming a pharmaceutically acceptable salt with a parent compound containing an acidic moiety include $Na^+$, $K^+$, $Ca^{2+}$, $Mg^{2+}$, $NH_4^+$, L-arginine, 2,2'-iminobisethanol, L-lysine, N-methyl-D-glucamine or tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. Salts of other acids than those mentioned above which for example are useful for purifying or isolating the compounds of the present invention (e.g. trifluoroacetate salts) also comprise a part of the invention.

BIOLOGICAL ASSAYS AND DATA

List of Abbreviations
DMEM Dulbecco's Modified Eagle's Medium
FBS fetal Bovine Serum
FLIPR fluorometric imaging plate reader
HEK293 cell line derived from human embryonic kidney cells
HEPES hydroxyethyl-piperazineethane-sulfonic acid buffer
IC50 half maximal inhibitory concentration
MDCK Madin-Darby canine kidney
MDR1 Multi drug resistance protein 1
P-gp p-Glycoprotein
SEM standard error mean
EGTA ethylene glycol-bis(β-aminoethyl ether)-N,N,N',N'-tetraacetic acid, also known as egtazic acid In-Vitro Effect:

Determination of In Vitro Pharmacological Activity

The activity of the compounds of the invention may be demonstrated using the following in vitro NMDA NR1/NR2B cell assays:

Method:

A human HEK293 cell line with tetracyclin-inducible expression of NMDA NR1/NR2B receptor was used as a test system for compound efficacy and potency. The cell line was purchased from ChanTest, Catalog #CT6121. Compound activity was determined by measuring the effect of compounds on intracellular calcium concentration induced by glycine/glutamate agonism in a FLIPRtetra system (Molecular Devices).

Cell Culture:

The cells were obtained as frozen cells in cryo-vials and stored until use at −150° C. Cells were grown in culture medium (DMEM/F12, 10% FBS, 5 μg/mL Blasticidin, 150 μg/mL Zeozin, 500 μg/mL Geneticin). It is important that density does not exceed 80% confluence. For sub-culturing the cells were detached from flasks by Versene. For the assay, cells were detached, washed twice with induction medium (DMEM/F12 without glutamine, 10% FBS, 2 μg/mL Tetracycline, 2 mM Ketamine) and seeded to 384 well pure coat amine plates (Becton Dickinson, 50000 cells per well in 50 μl) 48 h prior to assay in induction medium.

Compound Preparation

The test compounds were dissolved in 100% DMSO at a concentration of 10 mM and in a first step diluted in DMSO to a concentration of 5 mM, followed by serial dilution steps in 100% DMSO. Dilution factor and number of dilution steps may vary according to needs. Typically 8 different concentrations by 1:5 dilutions were prepared in duplicate, further intermediate dilutions (1:37.5) of the substances were carried out with aqueous assay buffer (137 mM NaCl, 4 mM KCl, 1.8 mM $CaCl_2$, 10 mM HEPES, 10 mM Glucose, pH 7.4) resulting in a compound concentration 3 times above the final test concentration and DMSO at 2.7% resulting in 0.9% final DMSO concentration in the assay.

FLIPR Assay:

At the assay day cells were washed 3× with assay buffer (as described above), 10 μL buffer remained in the wells after washing. 10 μL Ca kit loading buffer (AAT Bioquest; prepared from the kit containing the following components: Component A: Fluo-8 NW dissolved in 200 μL DMSO and 20 μl of this solution are mixed with 10 ml buffer prepared out of component B and C, Component B: 10× Pluronic® F127 Plus diluted 1:10 in component C, Component C: HHBS (Hanks with 20 mM Hepes) was added to the cells and the plates were incubated with lid for 60 minutes at room temperature. 20 μl assay buffer containing 60 μM glycine (20 μM final) and 3 μM glutamate (1 μM final) was added to column 1-23, column 24 got assay buffer without glycine/glutamate to serve as negative unstimulated control. Fluorescence (indicating the calcium influx as a result of the NR1/NR2B ion channel activation) was read on the FLIPRtetra device for 60 seconds to monitor the glutamate induced effects. After 2 minutes 20 μL of compound dilution prepared as described above or controls (row 1-22) in assay buffer were carefully added to the wells. Fluorescence was read on the FLIPR tetra device for additional 6 minutes to monitor the compound induced effects after activation by agonists. The average of 2 measurements at 5 minutes and 5 mM 10 seconds after compound addition is calculated and further used for IC50 calculations. Each assay microtiter compound dilution plate contained wells (in column 23 or 24) with DMSO controls instead of compound as controls for glycine/glutamate induced fluorescence (high controls)

and wells with 1 μM of a reference NR2B NAM as low controls (Compound 22; reference: Layton, Mark E et al, ACS Chemical Neuroscience 2011, 2(7), 352-362).

Data Evaluation and Calculation:

The output file of the reader contains the well number and measured average fluorescence units. For data evaluation and calculation, the measurement of the low control was set as 0% control and the measurement of the high control was set as 100% control. The IC50 values were calculated using the standard 4 parameter logistic regression formula. Calculation: $[y=(a-d)/(1+(x/c)^b)+d]$, a=low value, d=high value; x=conc M; c=IC50 M; b=slope.

NR2B negative allosteric modulators covered by general structure A and exhibiting a low $IC_{50}$ value are preferred.

TABLE 1

In vitro NR2B affinity of the compounds of the present invention as obtained in the FLIPR assay.

| Example number | $IC_{50}$ [nM] |
|---|---|
| 11 | 103 |
| 12 | 117 |
| 13 | 442 |
| 14 | 198 |
| 15 | 69 |
| 16 | 205 |
| 17 | 188 |
| 19 | 199 |
| 29 | 194 |
| 30 | 454 |
| 31 | 275 |
| 32 | 255 |
| 33 | 366 |
| 34 | 133 |
| 35 | 457 |
| 36 | 353 |
| 37 | 203 |
| 38 | 419 |
| 39 | 282 |
| 40 | 452 |
| 41 | 286 |

TABLE 2

In vitro NR2B affinity of the closest prior art compounds (examples 100, 105, 106 and 107 in WO2015/130905) as obtained in the same FLIPR assay as compounds in Table 1.

| Example number in WO2015/130905 | IC50 [nM] |
|---|---|
| 100 | >8887 |
| 105 | >9261 |
| 106 | >9255 |
| 107 | >9257 |

Determination of Nav 1.6.Inhibition

Equipment:

IonWorks Quattro electrophysiological platform

Compound Plate Preparation

The compounds were prepared in DMSO at 300× the final assay concentrations of 1 and 5 μM.

The 300×DMSO stock solutions were transferred into assay plates where 2 μl per well of each 300× stock solution were placed. All assay plates were stored at −80° C. until the day of assay.

On the day of the assay, the appropriate assay plate was thawed at room temperature, centrifuged, and 198 μl of external recording solution was added and mixed thoroughly. This provided a 1:100 dilution. A further 1:3 dilution occurred upon addition to the cells in the IonWorks Quattro electrophysiological platform, giving a 1:300 dilution in total. On each assay plate, at least 8 wells were reserved for vehicle control (0.3% DMSO) and at least 8 wells for each positive control specific to the cell line tested. The positive controls were tested at a maximal blocking and an approximate IC50 concentration. As positive control Lidocaine at concentrations of 30 and 1000 μM was used.

Electrophysiological Recording Solutions

The solutions for recording Nav1.6 currents were as follows:

External Recording Solution
NaCl 137 mM
KCl 4 mM
$MgCl_2$ 1 mM
$CaCl_2$ 1.8 mM
HEPES 10 mM
Glucose 10 mM
pH 7.3 (titrated with 10M NaOH)
Internal Recording Solution
CsF 90 mM
CsCl 45 mM
HEPES 10 mM
EGTA 10 mM
pH 7.3 (titrated with 1M CsOH)

Amphotericin B was used to obtain electrical access to the cell interior at a final concentration of 200 μg/ml in internal recording solution.

Experimental Protocols & Data Analysis

Nav1.6 Experimental Protocol

State-dependent inhibition: Sodium channels when held at depolarized potential or long test pulse, the channels open and inactivate and then stay inactivated until the membrane potential is stepped back to hyperpolarized potentials, when the inactivated channels recover from inactivation into closed state. An example is Tetracaine inhibition (FIG. 1), which is much stronger at depolarized potentials than at hyperpolarized potential.

Nav1.6 Data Analysis

Cells were held at −120 mV. In order to completely inactivate the sodium channels (pulse 1), the cells were pulsed to +0 mV for 2500 ms and stepped back to −120 mV for 10 ms (to completely recover from inactivation, however channels that had drugs bound to them will not recover from inactivation) before stepping to +0 mV for 20 ms (pulse 2).

IonChannel Profiler Data Filters

| Data Filter | Platform | Criteria |
|---|---|---|
| Seal Quality | IonWorks Quattro | >30 MΩ |
| Seal Drop | IonWorks Quattro | <50% Seal Drop (Seal Pre-Compound/Seal Post Compound) |
| Current Amplitude | IonWorks Quattro | >200 pA |

Assay Control Results

Both the positive and vehicle control data associated with each cell line assayed are shown below as an example. The mean is shown for each positive and negative control as solid symbol with the total number of individual well replicates given next to the solid symbol. In addition, the individual data of each well are shown on the graph as open symbols so that the variation about the mean value can be readily assessed. These data are provided to aid in determining whether a compound has activities on the ion channel relative to the control data and provides an indication of assay variability and accordingly is used to judge the effect size of a compound-specific effect that can be detected.

Shown below are the assay controls for the Nav1.6 IonWorks Quattro assay. Lidocaine, a Nav1.6 reference compound, inhibited evoked currents in a concentration and use dependent manner as predicted (FIG. 2).

Figure 2:
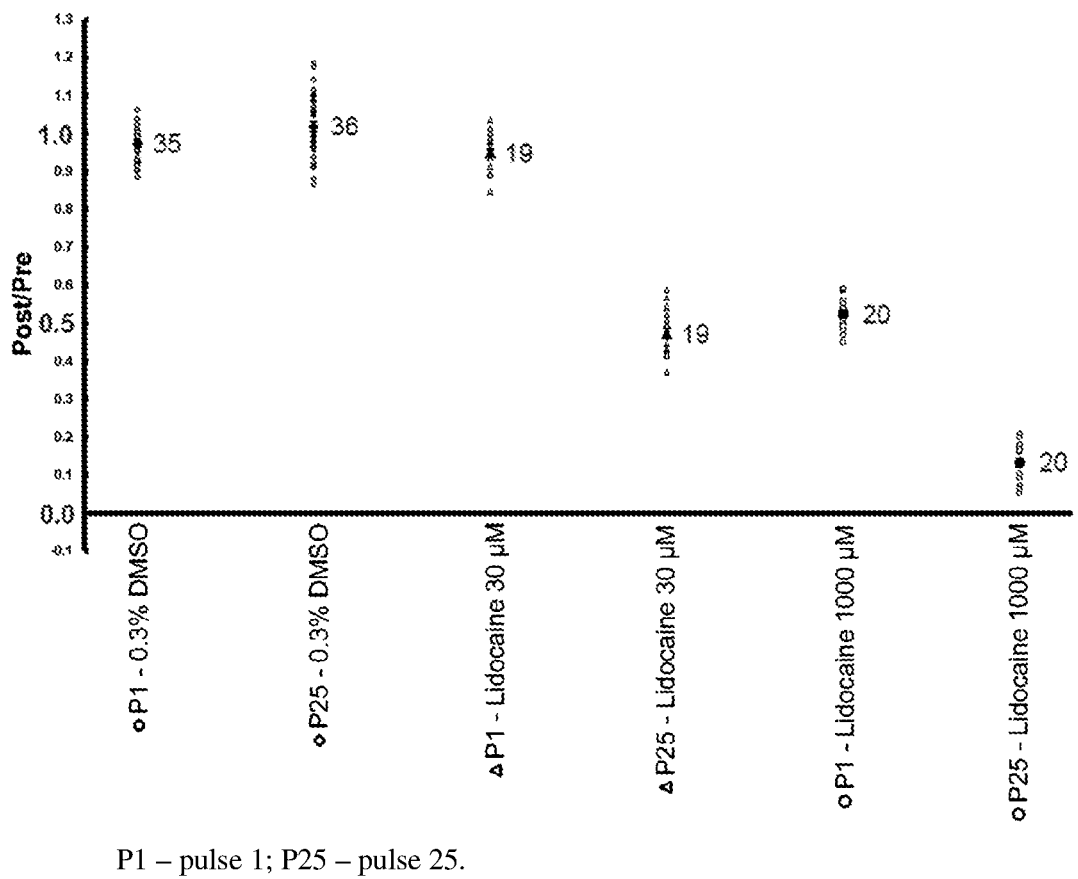
FIG. 2 shows the inhibition of evoked currents in a concentration and use dependent manner using Lidocaine as reference compound.

In FIG. 2, a Post/Pre value of 1.0 corresponds to 0% inhibition, a Post/Pre value of 0.0 corresponds to 100% inhibition. To illustrate the variation of the assay, both example 106 of WO2015/130905 showing 14% inhibition of Nav 1.6 at 5 µM (normalized, see Table 3) and example 19 of the present invention showing −6.3% inhibition of Nav 1.6 at 5 µM (normalized, see Table 4), respectively, are within the variation of the assay when compared to assay control data, and are therefore not showing any significant inhibition of the Nav 1.6 channel at 5 µM.

Tables 3 and 4 show the normalized percentage inhibition of Nav1.6 channel. The normalized data show the compound data normalized to vehicle control (0% inhibition) and maximal inhibition control (100% inhibition); maximum inhibition at P1 by 1000 µM lidocaine (not normalized) was ranging from 46.4% to 47.2% across the experiments. (see also the figure Assay Control Results above).

TABLE 3

Normalized in vitro Nav 1.6 inhibition of the closest prior art compounds (examples 100, 105, 106 and 107 in WO2015/130905) as obtained in the same electrophysiology assay as compounds in Table 4 (concentrations: 1 µM and 5 µM).

| Example number in WO2015/130905 | Normalized % inhibition at 1 µM | Normalized % inhibition at 5 µM | Percentage SEM at 1 µM | Percentage SEM at 5 µM |
| --- | --- | --- | --- | --- |
| 100 | 2.2 | 37.8 | 6.2 | 8.4 |
| 105 | 18.2 | 68 | 2.6 | 4.1 |
| 106 | −0.7 | 14 | 1.6 | 0.4 |
| 107 | −8.5 | 13.1 | 3.9 | 2.8 |

TABLE 4

Normalized in vitro Nav 1.6 inhibition of the compounds of the present invention as obtained in the same electrophysiology assay as prior art compounds in Table 3 (concentrations: 1 µM and 5 µM).

| Example number | Normalized % inhibition at 1 µM | Normalized % inhibition at 5 µM | Percentage SEM at 1 µM | Percentage SEM at 5 µM |
| --- | --- | --- | --- | --- |
| 11 | 4.2 | −3.6 | 2.7 | 3.9 |
| 12 | 5.1 | 10.2 | 3.9 | 0.7 |
| 13 | −3.1 | −1.8 | 1.0 | 6.6 |
| 14 | 0.7 | 0.4 | — | 2.5 |
| 15 | −17.4 | −1.4 | 5.5 | 3.4 |
| 16 | −0.5 | 7.1 | 2.1 | 4.4 |
| 17 | 22 | −4.3 | 4.3 | 4.2 |
| 19 | 5.2 | −6.3 | 1.4 | — |
| 29 | 1.8 | 3.0 | 3.4 | 2.5 |
| 30 | 7.6 | 6.8 | 0.7 | 3.6 |

NR2B negative allosteric modulators covered by general structure A which are not showing any significant Nav1.6 inhibition are preferred.

The compounds of the present invention do not show any significant inhibition of the Nav 1.6 channel at 1 and 5 µM, respectively (see Table 4 and Assay Control Results), whereas examples 100 and 105 of WO2015/130905 show 37.8% and 68% inhibition of Nav 1.6 at 5 µM (see Table 3). Examples_106 and 107 of WO2015/130905 do not show any significant inhibition of the Nav 1.6 channel at 1 and 5 µM, respectively (i.e. inhibition is within assay variability, see Table 3 and Assay Control Results).

MDCK Assay P-gp

Apparent permeability coefficients (Papp) of the compounds across the MDCK-MDR1 monolayers (MDCKII cells transfected with human MDR1 cDNA expression plasmid) are measured in apical-to-basal (AB) and basal-to-apical (BA) direction. MDCK-MDR1 cells ($6 \times 10^5$ cells/cm$^2$) are seeded on filter inserts (Corning, Transwell, polycarbonate, 0.4 µm pore size) and cultured for 9 to 10 days. Compounds dissolved in DMSO stock solution (1-20 mM) are diluted with HTP-4 aqueous buffer (128.13 mM NaCl, 5.36 mM KCl, 1 mM MgSO$_4$, 1.8 mM CaCl$_2$, 4.17 mM NaHCO$_3$, 1.19 mM Na$_2$HPO$_4$, 0.41 mM NaH$_2$PO$_4$, 15 mM HEPES, 20 mM glucose, pH 7.4) supplemented with 0.25% BSA to prepare the transport solutions (final concentration: 1 or 10 µM, final DMSO<=0.5%). The transport solution is applied to the apical or basolateral donor side for measuring A-B or B-A permeability, respectively. The receiver side contains HTP-4 buffer supplemented with 0.25% BSA. Samples are collected at the start and end of experiment from the donor and at various time intervals for up to 2 hours also from the receiver side for concentration measurement by HPLC-MS/MS (RapidFire High-throughput MS System (Agilent) coupled to QTrap 6500 (AB Sciex) or TSQ Vantage (Thermo Scientific)). Sampled receiver volumes are replaced with fresh receiver solution. Efflux ratio is calculated dividing the Papp (b-a) values by the Papp (a-b) values. Results are shown in Table 5.

TABLE 5

| Ex. | Papp (a-b) mean [10−6 cm/s] | efflux ratio PEBA/PEAB |
| --- | --- | --- |
| 11 | 72 | 0.6 |
| 12 | 80 | 0.7 |
| 13 | 45 | 1.0 |
| 14 | 92 | 0.4 |
| 15 | 42 | 0.7 |
| 16 | 51 | 0.7 |
| 17 | 67 | 0.6 |
| 19 | 75 | 0.7 |
| 29 | 58 | 0.8 |
| 30 | 86 | 0.5 |
| 31 | 63 | 0.7 |
| 32 | 80 | 0.5 |
| 33 | 71 | 0.5 |
| 34 | 58 | 0.8 |

The experimental results above show that compounds of the present invention are potent NR2B NAMs having high membrane permeability and no in vitro efflux anticipating excellent capability to cross the blood brain barrier.

Metabolic Stability

The metabolic degradation of the test compound was assayed at 37° C. with pooled human liver microsomes. The final incubation volume of 60 µl per time point contains TRIS buffer pH 7.6 at room temperature (0.1 M), magnesium chloride (5 mM aqueous solution), microsomal protein (1 mg/mL for human) and the test compound at a final concentration of 1 µM. Following a short preincubation period at 37° C., the reactions were initiated by addition of betanicotinamide adenine dinucleotide phosphate, reduced form (NADPH, 1 mM), and terminated by transferring an aliquot into acetonitril after different time points. After centrifugation (10000 g, 5 min), an aliquot of the supernatant was assayed by HPLC-MS/MS as described above for the MDCK assay P-gp for the amount of parent compound.

The half-life was determined by the slope of the semi-logarithmic plot of the concentration-time profile. Results are shown in Table 6.

TABLE 6

| Ex. | Half-life - t½ [min] human liver microsomes |
|---|---|
| 11 | >130 |
| 12 | >130 |
| 13 | >130 |
| 14 | >130 |
| 15 | >130 |
| 16 | >130 |
| 17 | >130 |
| 19 | >130 |
| 29 | >130 |
| 30 | >130 |
| 31 | >130 |
| 32 | >130 |
| 33 | >130 |
| 34 | >130 |

The experimental results above show that compounds of the present invention are potent NR2B NAMs having high stability in human liver microsomes.

The present invention provides compounds according to formula A that unexpectedly result in a favorable combination of the following key parameters:
1) potent and selective negative allosteric modulation of NR2B,
2) high stability in human liver microsomes, and
3) high permeability and no in vitro efflux at MDCK-MDR1 cell transporters.

Pharmaceutical Composition

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) may vary in the range from 0.1 to 95 wt.-%, preferably 5.0 to 90 wt.-% of the composition as a whole.

Suitable tablets may be obtained, for example, by mixing a compound of the present invention with known excipients, for example inert diluents, carriers, disintegrants, adjuvants, surfactants, binders and/or lubricants and pressing the resulting mixture to form tablets.

Use in Treatment/Method of Use

Human therapeutic applications of NR2B NAM have been summarized in reviews by Traynelis et al. (Traynelis et al., Pharmacology Reviews, 2010, 62:405), Beinat et al. (Beinat et al., Current Medicinal Chemistry, 2010, 17:4166) and Mony et al. (Mony et al., British J. Pharmacology, 2009, 157:1301).

The present invention relates to compounds which are useful in the treatment of psychiatric disorders, diseases and conditions wherein negative allosteric modulation of NR2B is of therapeutic benefit, including: (1) mood disorders and mood affective disorders; (2) schizophrenia spectrum disorders; (3) neurotic, stress-related and somatoform disorders including anxiety disorders; (4) disorders of psychological development; (5) behavioral syndromes associated with physiological disturbances and physical factors; (6) substance-related and addictive disorders; (7) disease associated with symptoms of negative and positive valence; (8) pain; (9) cerebrovascular diseases; (10) episodic and paroxysmal disorders; (11) neurodegenerative diseases.

In view of their pharmacological effect, compounds of the present invention are suitable for use in the treatment of a disorder, disease or condition selected from the list consisting of (1) treatment of mood disorders and mood affective disorders including bipolar disorder I depressed, hypomanic, manic and mixed form; bipolar disorder II; depressive disorders, such as single depressive episode or recurrent major depressive disorder, minor depressive disorder, depressive disorder with postpartum onset, depressive disorders with psychotic symptoms; major depressive disorder with or without concomitant anxious distress, mixed features, melancholic features, atypical features, mood-congruent psychotic features, mood-incongruent psychotic features, catatonia.

(2) treatment of mood disorders belonging to the schizophrenia spectrum and other psychotic disorders including schizophrenia and schizoaffective disorder with associated negative and cognitive symptoms.

(3) treatment of disorders belonging to the neurotic, stress-related and somatoform disorders including anxiety disorders, general anxiety disorder, panic disorder with or without agoraphobia, specific phobia, social phobia, chronic anxiety disorders; obsessive compulsive disorder; reaction to sever stress and adjustment disorders, such as post-traumatic stress disorder; other neurotic disorders such as depersonalisation-derealisation syndrome.

(4) treatment of disorders of psychological development including pervasive developmental disorders, including Asperger's syndrome and Rett's syndrome, autistic disorders, childhood autism and overactive disorder associated with mental retardation and stereotyped movements, specific developmental disorder of motor function, specific developmental disorders of scholastic skills, attention deficit/hyperactivity disorder.

(5) treatment of behavioral syndromes associated with physiological disturbances and physical factors including mental and behavioural disorders associated with the puerperium, including postnatal and postpartum depression; eating disorders, including anorexia nervosa and bulimia nervosa and other impulse control disorders.

(6) treatment of disorders of substance-related and addicitive disorders, which are substance use disorders induced by alcohol, cannabis, hallucinogen, stimulant, hypnotic, tobacco.

(7) treatment of disease associated with symptoms of negative and positive valence including anhedonia, sustained threat and loss, suicidal ideation.

(8) treatment of acute and chronic pain which is related to neuropathy, e.g. diabetic neuropathy or polyneuropathy, physiological processes and physical disorders including e.g. low back pain, pain in the joints, disease of the musculoskeletal system and connective tissue, e.g. rheumatism, myalgia, nerve, nerve root and plexus disorders, e.g. phantom limb syndrome with pain, carpal tunnel syndrome.

(9) treatment of cerebrovascular diseases, e.g. intracerebral or subararchnoid haemorrhage, cerbral infarction, stroke, occlusion and stenosis, cerebral atherosclerosis, cerebral amyloid angiopathy.

(10) treatment of episodic and paroxymal disorders, e.g. epilepsy.

(11) treatment of diseases which include forms of neurodegeneration, e.g. stroke, Alzheimer's disease and Huntingon's disease.

As used herein, unless otherwise noted, the terms "treating", "treatment" shall include the management and care of a human subject or human patient for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

According to another aspect, the present invention provides a compound of formula A or a pharmaceutically acceptable salt thereof for use in the treatment and/or prevention of the above mentioned conditions.

According to another aspect, the present invention provides a compound of formula A according to any one of the preceding aspects characterized in that the compound of formula A is used in addition to behavioural therapy, TMS (transcranial magnetic stimulation), ECT (electroconvulsive therapy) and other therapies.

Combination Therapy

Compounds according to the present invention can be combined with other treatment options known to be used in the art in connection with a treatment of any of the indications the treatment of which is in the focus of the present invention.

According to another aspect, the present invention provides a compound of formula A according to any one of the preceding aspects characterized in that the compound of formula A is administered in addition to treatment with one or more antidepressant selected from the list consisting of duloxetine, escitalopram, bupropion, venlafaxine, desvenlafaxine, sertraline, paroxetine, fluoxetine, vortioxetine, mirtazapine, citalopram, vilazodone, trazodone, amitriptyline, clomipramine, agomelatine, levomilnacipran, lithium, doxepin, nortriptyline. The term "antidepressant" shall mean any pharmaceutical agent or drug which can be used to treat depression or diseases assocaited with depressive symptoms.

According to another aspect, the present invention provides a compound of formula A according to any one of the preceding aspects characterized in that the compound of formula A is administered in addition to treatment with one or more antipsychotic selected from the list consisting of aripiprazole, paliperidone palmitate, lurasidone, quetiapine, risperidone, olanzapine, paliperidone, brexpiprazole, clozapine, asenapine, chlorpromazine, haloperidol, cariprazine, ziprasidone, amisulpride, iloperidone, fluphenazine, blonanserin, aripiprazole lauroxil. The term "antipsychotic" shall mean any pharmaceutical agent or drug which can be used to treat diseases associated with psychotic or depressive symptoms.

According to another aspect, the present invention provides a compound of formula A according to any one of the preceding aspects characterized in that the compound of formula A is administered in addition to treatment with one or more psychostimulant selected from the list consisting of lisdexamfetamine, methylphenidate, amfetamine, dexamfetamine, dexmethylphenidate, armodafinil, modafinil The term "psychostimulant" shall mean any pharmaceutical agent or drug which can be used to treat diseases like mood disorders, or impulse control disorders.

According to another aspect, the present invention provides a compound of formula A according to any one of the preceding aspects characterized in that the compound of formula A is administered in addition to treatment with nootropics selected from the list consisting of oxiracetam, piracetam, or the natural product St John's-wort.

According to another aspect, the present invention provides a compound of formula A which is administered in addition to treatment with one or more antidepressant, antipsychotic, psychostimulant, nootropics or natural product according to any one of the preceding aspects characterized in that the combination of compound of formula A and one or more antidepressant, antipsychotic, psychostimulant, nootropics or natural product is used in addition to behavioural therapy, TMS (transcranial magnetic stimulation), ECT (electroconvulsive therapy) and other therapies.

EXPERIMENTAL SECTION

Abbreviations:
ACN acetonitrile
APCI Atmospheric pressure chemical ionization
Boc tert-butyloxycarbonyl
CDI 1,1'-carbonyldiimidazole
$CO_2$ Carbon Dioxide
D day
DA Diode Array
DCM dichloromethane
DIPE diisopropylether
DIPEA diisopropylethylamine
DMF dimethylformamide
e.e. enantiomeric excess
ESI electrospray ionization (in MS)
EtOAc ethylacetate
EtOH ethanol
Ex. example
h hour(s)
HATU O-(7-azabenzotriazol-1-yl)-N,N,N',N'-tetramethyl-uronium-hexafluorophosphate
HPLC high performance liquid chromatography
HPLC-MS coupled high performance liquid chromatography-mass spectrometry
M molar (mol/L)
MeOH methanol
min minute(s)
MS mass spectrometry
MW molecular weight
NH3 ammonia
PSI Pound per square inch
rt room temperature
$R_t$ retention time
scCO2 supercritical $CO_2$
solv solvent
TBTU O-(benzotriazol-1-yl)-N,N,N',N'-tetramethyluronium tetrafluoroborate
TEA triethylamine
TFA trifluoroacetic acid
THF tetrahydrofuran
TLC thin-layer chromatography
SFC Supercritical fluid chromatography
   Abbreviations within Spectral Data:
1H-NMR Proton nuclear magnetic resonance
br broad
δ chemical shift
d doublet
dd doublet of doublets
dt doublet of triplets
DMSO-$d_6$ hexa-deutero-dimethylsulfoxide
H proton
Hz Hertz (=1/second)
J coupling constant m multiplet
ppm parts per million
q quartet
s singlet
t triplet
td triplet of doublets General Analytics.

All reactions were carried out using commercial grade reagents and solvents. NMR spectra were recorded on a Bruker AVANCE IIIHD 400 MHz instrument using TopSpin 3.2 p16 software. Chemical shifts are given in parts per million (ppm) downfield from internal reference trimethylsilane in δ units. Selected data are reported in the following manner: chemical shift, multiplicity, coupling constants (J), integration. Analytical thin-layer chromatography (TLC) was carried out using Merck silica gel 60 F254 plates. All compounds were visualized as single spots using short wave UV light. Low resolution mass spectra were obtained using a liquid chromatography mass spectrometer (LCMS) that consisted of an Agilent 1100 series LC coupled to a Agilent 6130 quadrupole mass spectrometer (electrospray positive ionization).

Methods:
HPLC-MS methods:
Method 1

| Method Name: | Z003_S05 |
| --- | --- |
| Device description: | Agilent 1200 with DA- and MS-Detector |
| Column: | XBridge C18_3.0 × 30 mm_2.5 μm |
| Column producer: | Waters |
| Description: | |

| Gradient/Solvent Time [min] | % Sol [Water 0.1% $NH_3$] | % Sol [Acetonitrile] | Flow [ml/min] | Temp [° C.] | Back pressure [PSI] |
| --- | --- | --- | --- | --- | --- |
| 0.0 | 95.0 | 5.0 | 2.2 | 60.0 | |
| 0.2 | 95.0 | 5.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 3.0 | 60.0 | |

Method 2

| Method Name: | Z011_S03 |
| --- | --- |
| Device description: | Agilent 1200 with DA- and MS-Detector |
| Column: | XBridge C18_3.0 × 30 mm_2.5 μm |
| Column producer: | Waters |
| Description: | |

| Gradient/Solvent Time [min] | % Sol [Water 0.1% $NH_3$] | % Sol [Acetonitrile] | Flow [ml/min] | Temp [° C.] | Back pressure [PSI] |
| --- | --- | --- | --- | --- | --- |
| 0.0 | 97.0 | 3.0 | 2.2 | 60.0 | |
| 0.2 | 97.0 | 3.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 3.0 | 60.0 | |

Method 3

| Method Name: | Z017_S04 |
| --- | --- |
| Device description: | Agilent 1200 with DA- and MS-Detector |
| Column: | Sunfire C18_3.0 × 30 mm_1.8 μm |
| Column producer: | Waters |
| Description: | |

| Gradient/Solvent Time [min] | % Sol [Water 0.1% TFA] | % Sol [Acetonitrile] | Flow [ml/min] | Temp [° C.] | Back pressure [PSI] |
| --- | --- | --- | --- | --- | --- |
| 0.0 | 97.0 | 3.0 | 2.2 | 60.0 | |
| 0.2 | 97.0 | 3.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 3.0 | 60.0 | |

Chiral SFC Analytical Methods:
Method 4: G_IG_IPA_$NH_3$_001

| Method Name: | G_IG_IPA_$NH_3$_001 |
| --- | --- |
| Device description: | Agilent 1260 SFC with DAD and MS |
| Column: | CHIRALPAK ® IG_4.6 × 250 mm_5 μm |
| Column producer: | Daicel |

| Gradient/Solvent Time [min] | % Sol [scCO2] | % Sol [IPA 20 mM $NH_3$] | Flow [ml/min] | Temp [° C.] | Back pressure [PSI] |
| --- | --- | --- | --- | --- | --- |
| 0.0 | 95.0 | 5.0 | 4.0 | 40.0 | 2175.0 |
| 9.0 | 40.0 | 60.0 | 4.0 | 40.0 | 2175.0 |
| 10.0 | 40.0 | 60.0 | 4.0 | 40.0 | 2175.0 |

Method 5: G_IG_MeOH_$NH_3$_001

| Method Name: | G_IG_MeOH_$NH_3$_001 |
| --- | --- |
| Device description: | Agilent 1260 SFC with DAD and MS |
| Column: | CHIRALPAK ® IG_4.6 × 250 mm_5 μm |
| Column producer: | Daicel |

| Gradient/Solvent Time [min] | % Sol [scCO2] | % Sol [MeOH 20 mM $NH_3$] | Flow [ml/min] | Temp [° C.] | Back pressure [PSI] |
| --- | --- | --- | --- | --- | --- |
| 0.0 | 95.0 | 5.0 | 4.0 | 40.0 | 2175.0 |
| 9.0 | 40.0 | 60.0 | 4.0 | 40.0 | 2175.0 |
| 10.0 | 40.0 | 60.0 | 4.0 | 40.0 | 2175.0 |

Method 6: G_C4_MeOH_$NH_3$_001

| Method Name: | G_C4_MeOH_$NH_3$_001 |
| --- | --- |
| Device description: | Agilent 1260 SFC with DAD and MS |
| Column: | LUX ® Cellulose-4 6 × 250 mm_5 μm |
| Column producer: | Phenomenex |

| Gradient/Solvent Time [min] | % Sol [scCO2] | % Sol [MeOH 20 mM $NH_3$] | Flow [ml/min] | Temp [° C.] | Back pressure [PSI] |
| --- | --- | --- | --- | --- | --- |
| 0.0 | 95.0 | 5.0 | 4.0 | 40.0 | 2175.0 |
| 9.0 | 40.0 | 60.0 | 4.0 | 40.0 | 2175.0 |
| 10.0 | 40.0 | 60.0 | 4.0 | 40.0 | 2175.0 |

Method 7: I_SA_20_MEOH_NH₃_001

| Method Name: | I_SA_20_IPA_NH₃_001 |
|---|---|
| Device description: | Agilent 1260 SFC with DAD and MS |
| Column: | CHIRAL ART ® Amylose SA_4.6 × 250 mm_5 μm |
| Column producer: | YMC |

| Gradient/Solvent Time [min] | % Sol [scCO2] | % Sol [ETOH 20 mM NH₃] | Flow [ml/min] | Temp [° C.] | Back pressure [PSI] |
|---|---|---|---|---|---|
| 0.0 | 80.0 | 20.0 | 4.0 | 40.0 | 2175.0 |
| 10.0 | 80.0 | 20.0 | 4.0 | 40.0 | 2175.0 |

Method 8: I_IC_30_IPA_NH₃_001

| Method Name: | I_IC_30_IPA_NH₃_001 |
|---|---|
| Device description: | Agilent 1260 SFC with DAD and MS |
| Column: | Chiralpak ® IC_4.6 × 250 mm_5 μm |
| Column producer: | Daicel |

| Gradient/Solvent Time [min] | % Sol [scCO2] | % Sol [MEOH 20 mM NH₃] | Flow [ml/min] | Temp [° C.] | Back pressure [PSI] |
|---|---|---|---|---|---|
| 0.0 | 70.0 | 30.0 | 4.0 | 40.0 | 2175.0 |
| 10.0 | 7.0 | 30.0 | 4.0 | 40.0 | 2175.0 |

Microwave equipment: Biotage Initiator⁺

Preparative HPLC Method for Purification:

Instrument: (Agilent 1100). Eluents: Water—NH₄OH 5% solution in Water—CH₃CN;

Flow: 50 ml/min; Temperature 60° C.; Column: XBridge C18.

Preparation of Intermediates:

Example 1a

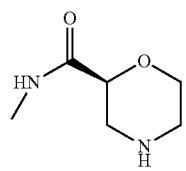

(S)-Morpholine-2-carboxylic acid methyl ester hydrochloride (35.0 g; 193 mmol) was mixed together with 400 ml of a 8M solution of Methylamine in EtOH. The reaction mixture was stirred at room temperature over 60 hours. The solvent was removed under reduced pressure, THF (500 ml) and TEA (50 ml) were added and the reaction mixture stirred at room temperature during 12 hours. A precipitate was formed; the suspension was filtered via a glass filter and the filtrate solution was evaporated under reduced pressure. Obtained 23.5 g of the desired product as solid.

Example 1a

Chiral SFC Method: I_IC_30_IPA_NH₃_001.M
R$_t$ [min]: 3.72; e.e. 100%
MS: 145 (M+H)⁺

Example 5a

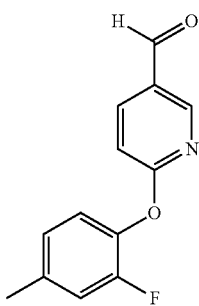 [SMILES: Cc1ccc(Oc2ccc(C=O)cn2)c(F)c1]

6-Chloro-pyridine-3-carbaldehyde (1.50 g; 10.6 mmol) and 2,4-difluoro-phenol (1.22 ml; 12.7 mmol) are dissolved in DMF (10 ml) in a microwave vial; K₂CO₃ (2.20 g; 15.9 mmol) is added and the reaction mixture is stirred at 110° C. during 30 minutes. The reaction mixture is then partitioned between Ethyl Acetate (150 ml) and Water (80 ml); the organic phase is separated and washed with a solution of K₂CO₃ (10% in water) and the dried over Na₂SO₄. The crude product obtained after evaporation of the solvent is purified by flash-chromatography (Eluent: Petrol Ether/Ethyl Acetate 4/1). Obtained 2.3 g of the desired compound (content 70%) used as such in the next step.

Example 5a

HPLC-MS (Method): Z017_S04R$_t$ [min]: 0.98
MS: 236 [M+H]⁺

Example 5b

Example 5b was synthesised in analogy to Example 5a. Starting materials: 6-Chloro-pyridine-3-carbaldehyde (1.50 g; 10.6 mmol) and 2-fluoro-4-methylphenol (1.38 ml; 12.7 mmol).

The crude obtained after work up was passed through a silica pad (Eluent: Petrol Ether/Ethyl Acetate 4/1). Obtained 1.60 g of the desired compound (content 50%) used as such in the next step.

Example 5b

HPLC-MS (Method): Z017_S04 $R_t$ [min]: 1.02
MS: 232 [M+H]$^+$

Example 5c

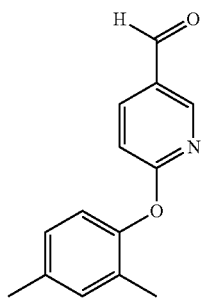 [SMILES: Cc1ccc(Oc2ccc(C=O)cn2)c(C)c1]

Example 5c was synthesised in analogy to Example 5a. Starting materials: 6-Chloro-pyridine-3-carbaldehyde (1.50 g; 10.6 mmol) and 2,-4-dimethylphenol (1.51 ml; 12.7 mmol).

The crude obtained after work up was passed through a silica pad (Eluent: Petrol Ether/Ethyl Acetate 4/1). Obtained 2.30 g of the desired compound (content 50%) used as such in the next step.

Example 5c

HPLC-MS (Method): Z017_S04 $R_t$ [min]: 1.06
MS: 228 [M+H]$^+$

Example 5d

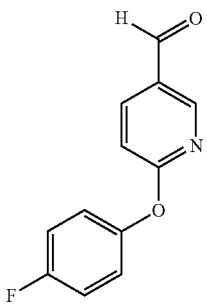 [SMILES: O=Cc1ccc(Oc2ccc(F)cc2)nc1]

Example 5d was synthesised in analogy to Example 5a. Starting materials: 6-Chloro-pyridine-3-carbaldehyde (1.50 g; 10.6 mmol) and 4-fluoro-phenol (1.43 g; 12.7 mmol).

Obtained 1.40 g of the desired compound used as such in the next step.

Example 5d

HPLC-MS (Method): Z017_S04 $R_t$ [min]: 0.94
MS: 218 [M+H]$^+$; 250 (M+H+MeOH)$^+$ Example 5e

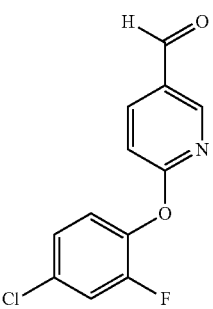 [SMILES: O=Cc1ccc(Oc2ccc(Cl)cc2F)nc1]

Example 5e was synthesised in analogy to Example 5a. Starting materials: 6-Chloro-pyridine-3-carbaldehyde (1.50 g; 10.6 mmol) and 2-fluoro-4-chloro-phenol (1.35 ml; 12.7 mmol).

Obtained 2.20 g of the desired compound (content 80-90%) used as such in the next step.

Example 5e

HPLC-MS (Method): Z017_S04 $R_t$ [min]: 1.05
MS: 252 and 254 [M+H]$^+$; Isotopic pattern for 1 Cl observed Example 5f

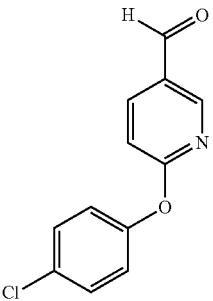 [SMILES: O=Cc1ccc(Oc2ccc(Cl)cc2)nc1]

Example 5f was synthesised in analogy to Example 5a. Starting materials: 6-Chloro-pyridine-3-carbaldehyde (1.50 g; 10.6 mmol) and 4-chloro-phenol (1.63 g; 12.7 mmol).

Obtained 2.40 g of the desired compound used as such in the next step.

Example 5f

HPLC-MS (Method): Z017_S04 $R_t$ [min]: 1.02
MS: 234 and 236 [M+H]$^+$; Isotopic pattern for 1 Cl observed Example 5g

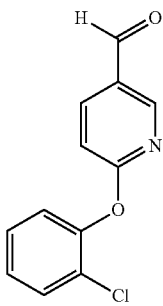 [SMILES: O=Cc1ccc(Oc2ccccc2Cl)nc1]

Example 5g was synthesised in analogy to Example 5a. Starting materials: 6-Chloro-pyridine-3-carbaldehyde (1.50 g; 10.6 mmol) and 2-chloro-phenol (1.29 ml; 12.7 mmol).

Obtained 2.40 g of the desired compound used as such in the next step.

Example 5g

HPLC-MS (Method): Z017_S04 $R_t$ [min]: 0.99
MS: 234 and 236
$[M+H]^+$; Isotopic pattern for 1 Cl observed Example 5h

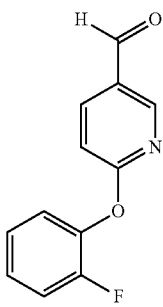 [SMILES: O=Cc1ccc(Oc2ccccc2F)nc1]

Example 5h was synthesised in analogy to Example 5a. Starting materials: 6-Chloro-pyridine-3-carbaldehyde (1.50 g; 10.6 mmol) and 2-fluoro-phenol (1.13 ml; 12.7 mmol).

Obtained 2.00 g of the desired compound used as such in the next step.

Example 5h

HPLC-MS (Method): Z017_S04 $R_t$ [min]: 0.95
MS: 218 $[M+H]^+$

Example 5i

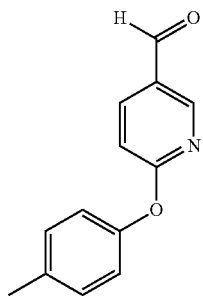 [SMILES: Cc1ccc(Oc2ccc(C=O)cn2)cc1]

Example 5i was synthesised in analogy to Example 5a. Starting materials: 6-bromo-pyridine-3-carbaldehyde (1.89 g; 10.2 mmol) and 4-methyl-phenol (1.10 g; 10.2 mmol).

Obtained 2.40 g of the desired compound (content 70%) used as such in the next step.

Example 5i

HPLC-MS (Method): Z017_S04 $R_t$ [min]: 0.95
MS: 214 $[M+H]^+$

Example 5j

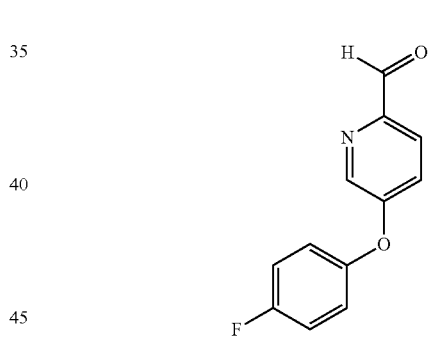

4-Fluoro-phenol (1.34 g; 12.0 mmol) was dissolved in DMSO (30 ml); potassium tert-butoxide (1.48 g; 13.2 mmol) was added at room temperature and the mixture was stirred for 1 h at room temperature. 5-Fluoro-2-formyl pyridine (1.50 g; 12.0 mmol) was then added and the reaction mixture was stirred at room temperature during 16 hours. 200 ml of a 1/1 mixture Dietyl ether/Ethyl Acetate was added followed by 70 ml of water. The phases were separated and the organic phase washed once more with water (20 ml). The organic phase was then dried over $Na_2SO_4$; the residue obtained after evaporation of solvents was purified by flash-chromatography employing as eluent Petrol Ether/Ethyl Acetate (ratio: 7/3). Obtained 1.80 g.

Example 5j

HPLC-MS (Method): Z017_S04 $R_t$ [min]: 0.90
MS: 218 $[M+H]^+$

Example 5k

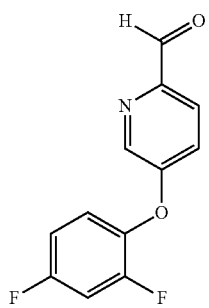

5-Fluoro-2-formyl pyridine (0.25 g; 2.00 mmol) and Cs$_2$CO$_3$ (0.98 g; 3.00 mmol) were suspended in DMF (10 ml); 2,4-difluoro-phenol (0.31 g; 2.40 mmol) was added and the reaction mixture was stirred at 80° C. during 3 hours. Acetonitrile (20 ml) was added and the mixture was filtered before being purified via preparative HPLC. Obtained 0.25 g of the desired compound.

Example 5k

HPLC-MS (Method):): Z011_S03; R$_t$ [min]: 0.96
MS: 236 [M+H]$^+$

Example 5l

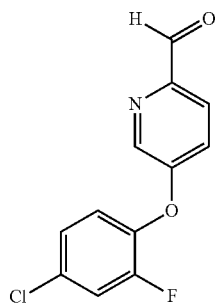 [SMILES: O=Cc1ccc(Oc2ccc(Cl)cc2F)cn1]

Example 5l was synthesised in analogy to example 5k. Starting materials: 5-Fluoro-2-formyl pyridine (0.25 g; 2.00 mmol) and 4-chloro-2-fluoro-phenol (0.26 ml; 2.40 mmol). Obtained: 0.35 g of the desired product.

Example 5l

HPLC-MS (Method):): Z011_S03; Rt [min]: 1.03
MS: 252 and 254 [M+H]$^+$;
Isotopic pattern for 1 Cl observed Example 5m

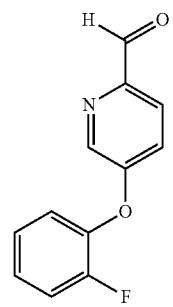 [SMILES: O=Cc1ccc(Oc2ccccc2F)cn1]

Example 5m was synthesised in analogy to example 5k. Starting materials: 5-Fluoro-2-formyl pyridine (0.25 g; 2.00 mmol) and 2-fluoro-phenol (0.21 ml; 2.40 mmol).
Obtained: 0.23 g of the desired product.

Example 5m

HPLC-MS (Method):): Z011_S03: Rt [min]: 0.94
MS: 218 [M+H]$^+$

Example 5n

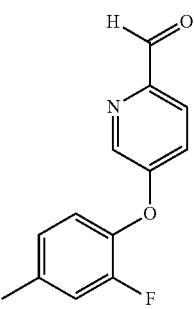 [SMILES: Cc1ccc(Oc2ccc(C=O)nc2)c(F)c1]

Example 5n was synthesised in analogy to example 5k. Starting materials: 5-Fluoro-2-formyl pyridine (0.25 g; 2.00 mmol) and 2-fluoro-4-methyl-phenol (0.30 g; 2.40 mmol).
Obtained: 0.34 g of the desired product.

Example 5n

HPLC-MS (Method): Z011_S03: R$_t$ [min]: 1.02
MS: 232 [M+H]$^+$

Example 5o

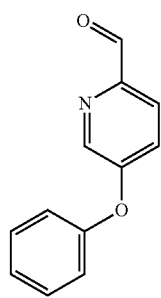 [SMILES: O=Cc1ccc(Oc2ccccc2)cn1]

5-Fluoro-2-formylpyridine (0.50 g; 4.00 mmol) and Phenol (0.45 g; 4.80 mmol) were dissolved in DMF (8 nal); $Cs_2CO_3$ (1.43 g; 4.40 mmol) was added and the reaction mixture was stirred at 80° C. during 16 hours. The reaction mixture was then partitioned between ethyl acetate (80 ml) and water (40 ml); the organic phase was separated and dried over $Na_2SO_4$. The crude product obtained after evaporation of the solvent was diluted with MeOH/H2O (10 mL), filtered and purified by preparative HPLC. Obtained 216 mg of the desired compound.

Example 5o

HPLC-MS (Method): Z017_S04: $R_t$ [min]: 0.94
MS: 200 [M+H]$^+$

Example 5p

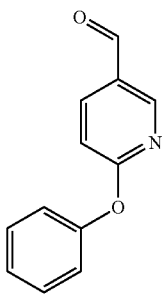 [SMILES: O=Cc1ccc(Oc2ccccc2)nc1]

6-Chloro-pyridine-3-carbaldehyde (1.50 g; 10.6 mmol) and Phenol (1.20 g; 12.7 mmol) were dissolved in DMF (10 ml) in a microwave vial; $K_2CO_3$ (2.20 g; 15.9 mmol) was added and the reaction mixture was stirred at 110° C. during 30 minutes. The reaction mixture was diluted with water (50 ml) and the obtained precipitate was filtered off, washed with water and dried in the air. Obtained 1.38 g of the desired compound.

Example 5p

HPLC-MS (Method): Z017_S04 $R_t$ [min]: 0.93
MS: 200 [M+H]$^+$

Example 5q

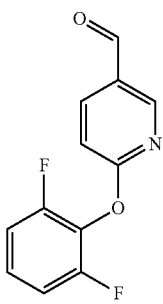 [SMILES: O=Cc1ccc(Oc2c(F)cccc2F)nc1]

6-Chloro-pyridine-3-carbaldehyde (1.50 g; 10.6 mmol) and 2,6-difluoro-phenol (1.65 g; 12.7 mmol) were dissolved in DMF (10 ml) in a microwave vial; $K_2CO_3$ (2.20 g; 15.9 mmol) was added and the reaction mixture was stirred at 110° C. during 30 minutes. The reaction mixture was then diluted with water (50 ml) and extracted with diethylether (70 ml). The organic phase was separated and dried over $Na_2SO_4$. The crude product obtained after evaporation was used as such in the next step. Obtained 2.30 g of the desired compound.

Example 5q

HPLC-MS (Method): Z017_S04 $R_t$ [min]: 0.98
MS: 236 [M+H]$^+$

Example 5r

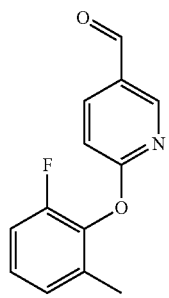 [SMILES: Cc1cccc(F)c1Oc1ccc(C=O)cn1]

Example 5r was synthesised in analogy to example 5q. Starting materials: 6-Chloro-pyridine-3-carbaldehyde (0.40 g; 2.83 mmol) and 2-fluoro-6-methyl-phenol (0.39 g; 3.11 mmol). Obtained: 0.43 g of the desired product (content 85%).

Example 5r

HPLC-MS (Method): Z017_S04: $R_t$ [min]: 1.01
MS: 232 [M+H]$^+$

Example 5s

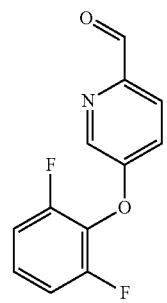 [SMILES: O=Cc1ccc(Oc2c(F)cccc2F)cn1]

5-Fluoro-2-formylpyridine (0.50 g; 4.00 mmol) and 2,6-Difluorophenol (0.62 g; 4.80 mmol) were dissolved in DMF (8 ml) in a microwave vial; $Cs_2CO_3$ (1.56 g; 4.80 mmol) was added and the reaction mixture was stirred at 80° C. during 16 hours. The reaction mixture was diluted with water (40 ml) and the obtained precipitate was filtered off, washed with water and dried in the air. Obtained 0.73 g of the desired compound (content 85%).

Example 5s

HPLC-MS (Method): Z017_S04 R$_t$ [min]: 0.97
MS: 236 [M+H]$^+$

Example 5t

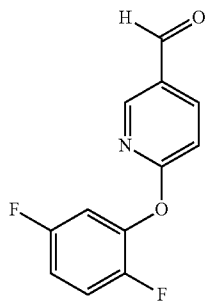 [SMILES: O=Cc1ccc(Oc2cc(F)ccc2F)nc1]

6-Chloro-pyridine-3-carbaldehyde (1.50 g; 10.6 mmol) and 2,5-difluoro-phenol (1.65 g; 12.7 mmol) were dissolved in DMF (10 ml) in a microwave vial; K$_2$CO$_3$ (2.20 g; 15.9 mmol) is added and the reaction mixture is stirred at 110° C. during 30 minutes. Water (50 ml) was added and the reaction mixture stirred over 30 min. The precipitate obtained after filtration was washed a second time with water (20 ml), dried and used as such in the next step. Obtained 2.32 g of the desired compound.

Example 5t

HPLC-MS (Method): Z017_S04 R$_t$ [min]: 0.98
MS: 236 [M+H]$^+$

Example 5u

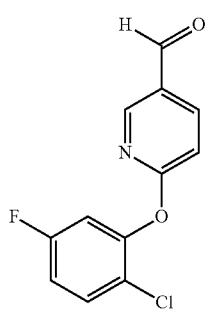 [SMILES: O=Cc1ccc(Oc2cc(F)ccc2Cl)nc1]

Example 5u was synthesised in analogy to Example 5t. Starting materials: 6-Chloro-pyridine-3-carbaldehyde (1.50 g; 10.6 mmol) and 2-chloro-5-difluoro-phenol (1.32 ml; 12.7 mmol). Obtained 2.4 g of the desired cpd.

Example 5u

HPLC-MS (Method): Z017_S04 R$_t$ [min]: 1.02
MS: 252 and 254 [M+H]$^+$;
isotopic pattern of 1 Cl observed

Exemplary Embodiments

Example 11

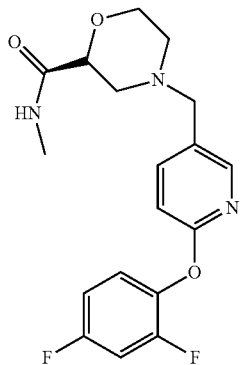

Example 1a (150 mg; content 70%; 0.45 mmol) and Example 5a (77.2 mg, 0.54 mmol) were dissolved in DMF; Acetic acid (0.08 ml; 1.34 mmol) and DIPEA (0.11 ml; 0.63 mmol) were added and the reaction mixture was stirred 30 min at 50° C.; NaBH(OAc)$_3$ (0.14 g; 0.67 mmol) was then added and the mixture was the stirred 22 hours at room temperature. The reaction mixture was then diluted with MeOH, filtered via a syringe filter and the obtained solution purified via preparative HPLC. Obtained 120 mg of the desired compound.

Example 11

HPLC-MS (Method): Z011_S03; R$_t$ [min]: 0.93
MS: 364 [M+H]$^+$
Chiral SFC Method: I_SA_20_IPA_NH$_3$_001
R$_t$ [min]: 1.83;
e.e. 100%
$^1$H NMR (400 MHz, DMSO-d$_6$); δ ppm: 1.89 (t, J=10.81 Hz, 1H); 2.06-2.14 (m, 1H); 2.57 (d, J=4.71 Hz, 3H); 2.63 (br d, J=11.17 Hz, 1H); 2.88 (br d, J=11.17 Hz, 1H); 3.40-3.59 (m, 3H); 3.82-3.89 (m, 2H); 7.09-7.16 (m, 1H); 7.11 (d, J=8.44 Hz, 1H); 7.36-7.45 (m, 2H); 7.67 (q, J=4.42 Hz, 1H); 7.81 (dd, J=8.42, 2.37 Hz, 1H); 7.99 (d, J=2.33 Hz, 1H).

Example 12

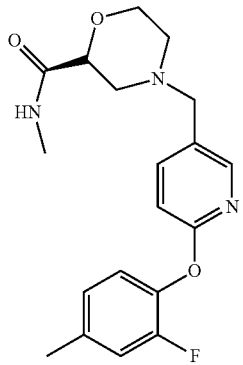

Example 12 was synthesised in analogy to example 11.

Starting materials: Example 5b (150 mg; content 50%; 0.32 mmol)+Example 1a (56.1 mg; 0.39 mmol).

The crude was purified by preparative HPLC. Obtained 105 mg of the desired compound.

Example 12

HPLC-MS Method: Z003_S05; $R_t$ [min]: 1.11

MS: 360 [M+H]$^+$

Chiral SFC Method: I_SA_20_IPA_NH$_3$_001

$R_t$ [min]: 2.39; e.e. 100%

$^1$H NMR (400 MHz, DMSO-d$_6$) δ ppm: 1.89 (t, J=10.81 Hz, 1H); 2.09 (br dd, J=11.47, 8.19 Hz, 1H); 2.33 (s, 3H); 2.54-2.59 (m, 3H); 2.60-2.65 (m, 1H); 2.88 (br d, J=11.28 Hz, 1H); 3.40-3.59 (m, 3H); 3.82-3.89 (m, 2H); 7.05 (t, J=10.04 Hz, 2H); 7.13-7.21 (m, 2H); 7.67 (br d, J=5.09 Hz, 1H); 7.78 (dd, J=8.42, 2.38 Hz, 1H); 7.97 (d, J=2.35 Hz, 1H).

Example 13

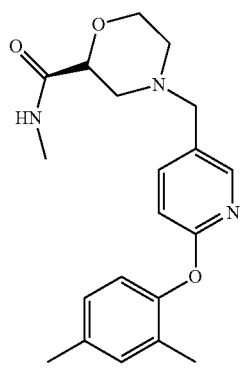

Example 13 was synthesised in analogy to example 11.

Starting materials: Example 5c (200 mg; content 50%; 0.44 mmol)+Example 1a (76.1 mg; 0.53 mmol).

The crude was purified by preparative HPLC. Obtained 119 mg of the desired compound.

Example 13

HPLC-MS Method: Z011_S03; $R_t$ [min]: 0.98

MS: 356 [M+H]$^+$

Chiral SFC Method: I_SA_20_IPA_NH$_3$_001

$R_t$ [min]: 2.95;

e.e. 100%

$^1$H NMR (400 MHz, DMSO-d$_6$); δ ppm: 1.88 (t, J=10.81 Hz, 1H); 2.00-2.12 (m, 1H); 2.03 (s, 3H); 2.28 (s, 3H); 2.53-2.59 (m, 3H); 2.60-2.65 (m, 1H); 2.89 (br d, J=11.28 Hz, 1H); 3.39-3.59 (m, 4H); 3.80-3.90 (m, 2H); 6.92 (dd, J=8.27, 1.87 Hz, 2H); 7.02 (dd, J=8.16, 2.22 Hz, 1H); 7.10 (s, 1H); 7.64-7.77 (m, 2H); 7.98 (d, J=2.38 Hz, 1H).

Example 14

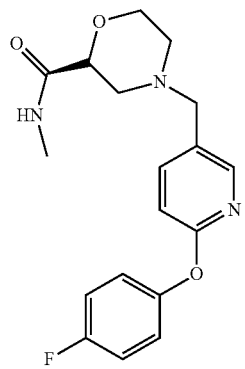

Example 14 was synthesised in analogy to example 11.

Starting materials: Example 5d (150 mg; 0.69 mmol)+Example 1a (119 mg; 0.83 mmol). The crude was purified by preparative HPLC.

Obtained 149 mg of the desired compound.

Example 14

HPLC-MS Method: Z003_S05; $R_t$ [min]: 1.05

MS: 346 [M+H]$^+$

Chiral SFC Method:: I_SA_20_IPA_NH$_3$_001

$R_t$ [min]: 2.23;

e.e. 100%

$^1$H NMR (400 MHz, DMSO-d$_6$); δ ppm: 1.89 (t, J=10.82 Hz, 1H); 2.11 (td, J=11.37, 3.33 Hz, 1H); 2.54-2.59 (m, 3H); 2.60-2.68 (m, 1H); 2.89 (dt, J=11.19, 2.12 Hz, 1H); 3.41-3.60 (m, 3H); 3.83-3.89 (m, 2H); 7.01 (d, J=8.40 Hz, 1H); 7.15-7.26 (m, 4H); 7.62-7.71 (m, 1H); 7.78 (dd, J=8.40, 2.39 Hz, 1H); 8.03 (s, 1H).

Example 15

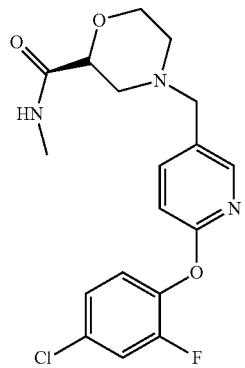

Example 15 was synthesised in analogy to example 11.

Starting materials: Example 5e (150 mg; content 85%; 0.51 mmol)+Example 1a (87.7 mg; 0.61 mmol). The crude was purified via preparative HPLC. Obtained 132 mg of the desired compound.

Example 15

HPLC-MS Method: Z003_S05; $R_t$ [min]: 1.14
  MS: 380 and 382
  [M+H]$^+$; isotopic pattern
  for 1 Cl observed
Chiral SFC Method: I_SA_20_IPA_NH$_3$_001
  $R_t$ [min]: 2.48; e.e. 100%
  $^1$H NMR (400 MHz, DMSO-d$_6$); δ ppm 1.89 (t, J=10.80 Hz, 1H); 2.06-2.14 (m, 1H); 2.52-2.59 (m, 3H); 2.60-2.65 (m, 1H); 2.88 (dt, J=11.22, 2.13 Hz, 1H); 3.41-3.60 (m, 3H); 3.81-3.90 (m, 2H); 7.13 (d, J=8.40 Hz, 1H); 7.31-7.41 (m, 2H); 7.60 (dd, J=10.46, 2.40 Hz, 1H); 7.64-7.70 (m, 1H); 7.82 (dd, J=8.42, 2.37 Hz, 1H); 7.99 (d, J=2.28 Hz, 1H).

Example 16

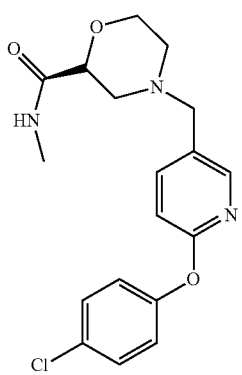

Example 16 was synthesised in analogy to example 11.

Starting materials: Example 5f (150 mg; 0.64 mmol)+Example 1a (111 mg; 0.77 mmol).

The crude was purified by preparative HPLC. Obtained 85 mg of the desired compound.

Example 16

HPLC-MS Method: Z003_S05; $R_t$ [min]: 1.12
  MS: 362 and 364 [M+H]$^+$;
  isotopic pattern for 1 Cl
  observed
Chiral SFC Method: I_SA_20_IPA_NH$_3$_001
  $R_t$ [min]: 3.21; e.e. 100%
  $^1$H NMR (400 MHz, DMSO-d$_6$); δ ppm 1.90 (t, J=10.81 Hz, 1H); 2.11 (td, J=11.38, 3.33 Hz, 1H); 2.56-2.67 (m, 4H); 2.90 (br d, J=11.29 Hz, 1H); 3.41-3.60 (m, 3H); 3.83-3.89 (m, 2H); 7.04 (d, J=8.37 Hz, 1H); 7.15-7.20 (m, 2H); 7.43-7.48 (m, 2H); 7.67 (q, J=4.63 Hz, 1H); 7.80 (dd, J=8.39, 2.40 Hz, 1H); 8.04 (d, J=2.38 Hz, 1H).

Example 17

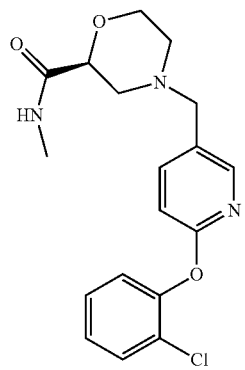 [SMILES: CNC(=O)[C@@H]1CN(Cc2ccc(Oc3ccccc3Cl)nc2)CCO1]

Example 17 was synthesised in analogy to example 11.

Starting materials: Example 5g (150 mg; content 90%; 0.58 mmol)+Example 1a (100 mg; 0.69 mmol).

The crude was purified by preparative HPLC. Obtained 191 mg of the desired compound.

Example 17

HPLC-MS Method: Z003_S05; $R_t$ [min]: 1.08
  MS: 362 and 364
  [M+H]$^+$; isotopic
  pattern for 1 Cl
  observed
Chiral SFC Method: I_SA_20_IPA_NH$_3$_001
  $R_t$ [min]: 2.75; e.e. 100%
  $^1$H NMR (400 MHz, DMSO-d$_6$); δ ppm: 1.89 (t, J=10.81 Hz, 1H); 2.05-2.16 (m, 1H); 2.52-2.67 (m, 4H); 2.89 (br d, J=11.43 Hz, 1H); 3.41-3.60 (m, 3H); 3.79-3.92 (m, 2H); 7.08 (d, J=8.39 Hz, 1H); 7.25-7.32 (m, 2H); 7.37-7.42 (m, 1H); 7.57 (dd, J=7.94, 1.58 Hz, 1H); 7.63-7.72 (m, 1H); 7.80 (dd, J=8.42, 2.38 Hz, 1H); 7.99 (d, J=2.36 Hz, 1H).

Example 19

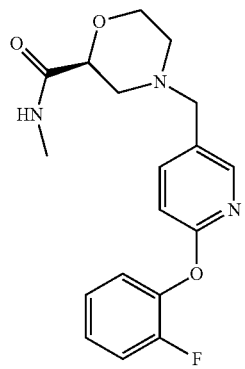 [SMILES: CNC(=O)[C@@H]1CN(Cc2ccc(Oc3ccccc3F)nc2)CCO1]

Example 19 was synthesised in analogy to example 11.

Starting materials: Example 5h (150 mg; 0.69 mmol)+Example 1a (119 mg; 0.83 mmol). The crude was purified by preparative HPLC. Obtained 147 mg of the desired compound.

Example 19

HPLC-MS Method: Z003_S05; $R_t$ [min]: 1.04

MS: 346 [M+H]$^+$

Chiral SFC Method: I_SA_20_IPA_NH$_3$_001

$R_t$[min]: 2.11; e.e.

100%

$^1$H NMR (400 MHz, DMSO-d$_6$); δ ppm: 1.89 (t, J=10.81 Hz, 1H); 2.10 (td, J=11.35, 3.25 Hz, 1H); 2.56-2.66 (m, J=4.71 Hz, 4H); 2.89 (br d, J=11.23 Hz, 1H); 3.41-3.60 (m, 3H); 3.83-3.89 (m, 2H); 7.10 (d, J=8.40 Hz, 1H); 7.21-7.37 (m, 4H); 7.62-7.72 (m, 1H); 7.80 (dd, J=8.42, 2.38 Hz, 1H); 7.99 (d, J=2.34 Hz, 1H).

Example 29

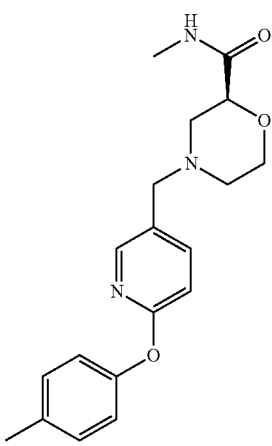 [SMILES: CNC(=O)[C@@H]1CN(Cc2ccc(Oc3ccc(C)cc3)nc2)CCO1]

Example 29 was synthesised in analogy to example 11.

Starting materials: Example 5i (250 mg; 60% content; 0.70 mmol) and Example 1a (127 mg; content 80%; 0.70 mmol). The crude was purified via preparative HPLC.

Obtained 174 mg of the desired product.

Example 29

HPLC-MS; Method: Z011_S03; $R_t$ [min]: 0.94

MS: 342 (M+H)$^+$

Chiral SFC Method:: I_SA_20_IPA_NH$_3$_001

$R_t$ [min]: 3.23; e.e.

99%

$^1$H NMR (400 MHz, DMSO-d$_6$); δ ppm: 1.89 (t, J=10.83 Hz, 1H); 2.06-2.14 (m, 1H); 2.30-2.33 (m, 3H); 2.54-2.67 (m, 4H); 2.86-2.92 (m, 1H); 3.40-3.59 (m, 3H); 3.83-3.89 (m, 2H); 6.93-7.02 (m, 3H); 7.20 (d, J=7.77 Hz, 2H); 7.64-7.70 (m, 1H); 7.75 (dd, J=8.46, 2.41 Hz, 1H); 8.02 (d, J=2.21 Hz, 1H).

Example 30

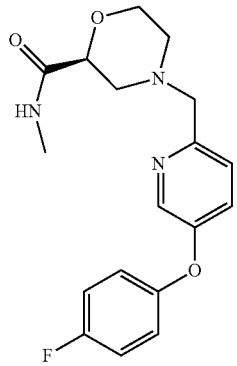 [SMILES: CNC(=O)[C@@H]1CN(Cc2ccc(Oc3ccc(F)cc3)cn2)CCO1]

Example 30 was synthesised in analogy to Example 11.

Starting materials: Example 5j (150 mg; 0.69 mmol) and Example 1a (124.5 mg; content 80%; 0.69 mmol). The crude was purified by preparative HPLC.

Obtained 157 mg of the desired compound.

Example 30

HPLC-MS; Method: Z011_S03; $R_t$ [min]: 0.89

MS: 346[M+H]$^+$

Chiral SFC Method:: I_SA_20_IPA_NH$_3$_001

$R_t$ [min]: 2.22; e.e.

100%

$^1$H NMR (400 MHz, DMSO-d$_6$) δ ppm: 1.98 (m, 1H); 2.18 (m, 1H); 2.55-2.59 (m, 3H); 2.64-2.71 (m, 1H); 2.95 (m, 1H); 3.55-3.65 (m, 3H); 3.84-3.91 (m, 2H); 7.11-7.16 (m, 2H); 7.22-7.28 (m, 2H); 7.37-7.47 (m, 2H); 7.68 (m, 1H) 8.28 (m, 1H).

Example 31

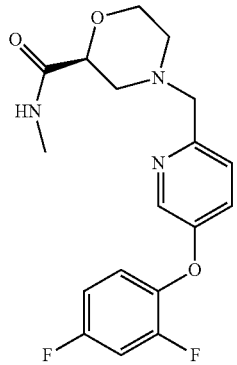 [SMILES: CNC(=O)[C@@H]1CN(Cc2ccc(Oc3ccc(F)cc3F)cn2)CCO1]

Example 1a (67.4 mg; 0.47 mmol) and example 5k (100 mg; 0.43 mmol) were dissolved in THF (3 ml); DIPEA (0.11 ml; 0.64 mmol) was added and the reaction mixture stirred 30 min before the addition of NaBH(OAc)3 (126 mg; 0.60 mmol). The mixture was stirred over 3 hours at room temperature, diluted with MeOH, filtered through a syringe filter and purified by preparative HPLC.

Obtained 53 mg of the desired compound.

Example 31

HPLC-MS; Method: Z003_S05; $R_t$ [min]: 1.074
  MS: 364 (M+H)$^+$
Chiral SFC Method:: G_IG_IPA_NH$_3$_001
  $R_t$ [min]: 5.75; e.e.
  94.8%
$^1$H NMR (400 MHz, DMSO-d$_6$) δ ppm: 1.98 (m, 1H); 2.18 (m, 1H); 2.57 (m, 3H); 2.62-2.71 (m, 1H); 2.93 (m, 1H); 3.54-3.66 (m, 3H); 3.83-3.92 (m, 2H); 7.12-7.18 (m, 1H); 7.33-7.53 (m, 4H); 7.60-7.72 (m, 1H); 8.29 (m, 1H).

Example 32

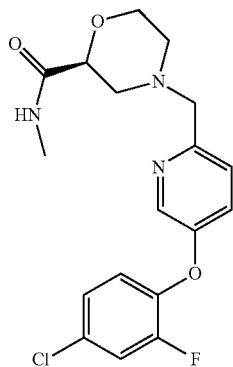 [SMILES: CNC(=O)[C@@H]1CN(Cc2ccc(Oc3ccc(Cl)cc3F)cn2)CCO1]

Example 32 was synthesised in analogy to example 31.
Starting materials: Example 5l (100 mg; 0.40 mmol) and Example 1a (63.0 mg; 0.44 mmol).
The crude was purified by preparative HPLC. Obtained 21 mg of the desired compound.

Example 32

HPLC-MS; Method: Z003_S05; $R_t$ [min]: 1.139
  MS: 380 and 382 [M+]$^+$;
  isotopic pattern for 1 Cl
  observed
Chiral SFC Method:: G_C4_MeOH_NH$_3$_001
  $R_t$ [min]: 4.26; e.e. 100%
$^1$H NMR (400 MHz, DMSO-d$_6$) δ ppm: 1.99 (m, 1H); 2.18 (m, 1H); 2.57 (m, 3H); 2.62-2.75 (m, 1H); 2.94 (m, 1H); 3.55-3.66 (m, 3H); 3.83-3.92 (m, 2H); 7.26-7.35 (m, 2H); 7.41-7.48 (m, 2H); 7.62-7.72 (m, 2H); 8.33 (m, 1H).

Example 33

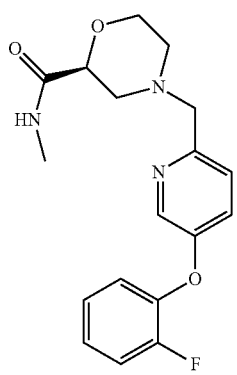 [SMILES: CNC(=O)[C@@H]1CN(Cc2ccc(Oc3ccccc3F)cn2)CCO1]

Example 33 was synthesised in analogy to example 31.
Starting materials: Example 5m (100 mg; 0.46 mmol) and Example 1a (73.0 mg; 0.51 mmol). The crude was purified by preparative HPLC. Obtained 42 mg of the desired compound.

Example 33

HPLC-MS; Method: Z003_S05; $R_t$ [min]: 1.056
  MS: 346 [M+H]$^+$
Chiral SFC Method:: G_IG_IPA_NH$_3$_001
  $R_t$ [min]: 6.41; e.e.
  100%
$^1$H NMR (400 MHz, DMSO-d$_6$) δ ppm: 1.99 (m, 1H); 2.18 (m, 1H); 2.58 (m, 3H); 2.63-2.70 (m, 1H); 2.94 (m, 1H); 3.55-3.65 (m, 3H); 3.84-3.91 (m, 2H); 7.23-7.33 (m, 3H); 7.34-7.50 (m, 4H); 7.67 (m, 1H); 8.30 (m, 1H).

Example 34

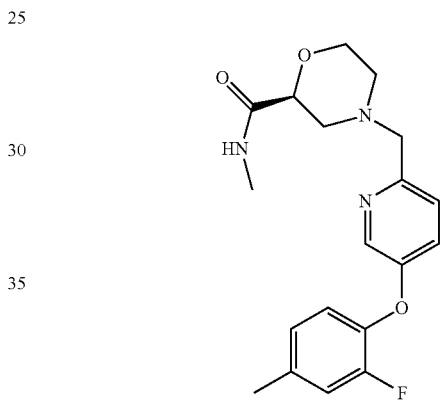

Example 34 was synthesised in analogy to example 31.
Starting materials: Example 5n (100 mg; 0.43 mmol) and Example 1a (74.8 mg; 0.52 mmol). The crude was purified by preparative HPLC.
Obtained 62 mg of the desired compound.

Example 34

HPLC-MS; Method: Z003_S05; $R_t$ [min]: 1.12
  MS: 360 [M+H]$^+$
Chiral SFC Method:: G_IG_MeOH_NH$_3$_001
  $R_t$ [min]: 5.96;
  e.e.:100%
$^1$H NMR (400 MHz, DMSO-d$_6$) δ ppm: 1.98 (m, 1H); 2.12-2.23 (m, 1H); 2.33 (s, 3H); 2.57 (m, 3H); 2.62-2.69 (m, 1H); 2.93 (m, 1H); 3.54-3.64 (m, 3H); 3.83-3.91 (m, 2H); 7.03-7.09 (m, 1H); 7.16 (m, 1H); 7.24 (m, 1H); 7.32 (m, 1H); 7.42 (m, 1H); 7.66 (m, 1H); 8.26 (m, 1H).

Example 35

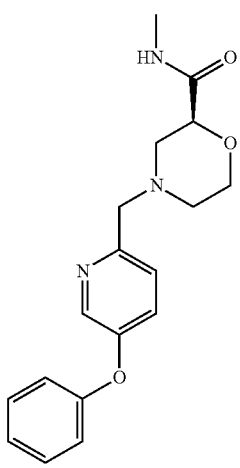 [SMILES: CNC(=O)[C@@H]1CN(Cc2ccc(Oc3ccccc3)cn2)CCO1]

Example 35 was synthesised in analogy to example 31.
Starting materials: Example 5o (100 mg; 0.50 mmol) and Example 1a (79.6 mg; 0.55 mmol). The mixture was stirred at room temperature overnight. The crude was purified by preparative HPLC. Obtained 95.0 mg of the desired compound.

Example 35

HPLC-MS; Method: Z011_S03; $R_t$ [min]: 0.88
  MS: 328 (M+H)$^+$
Chiral SFC Method:: I_SA_20_IPA_NH$_3$_001
  $R_t$ [min]: 2.5;
  e.e.: 100%
$^1$H NMR (400 MHz, DMSO-d$_6$) δ ppm 2.00 (m, 1H) 2.19 (m, 1H) 2.58 (m, 3H) 2.68 (m, 1H) 2.96 (m, 1H) 3.56-3.65 (m, 3H) 3.84-3.92 (m, 2H) 7.07 (m, 2H) 7.18 (m, 1H) 7.39-7.48 (m, 4H) 7.62-7.72 (m, 1H) 8.29 (m, 1H)

Example 36

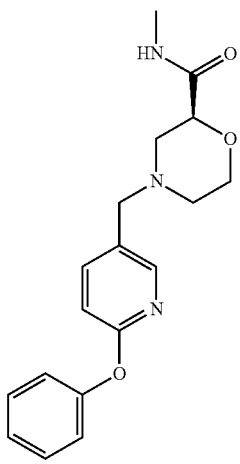 [SMILES: CNC(=O)[C@@H]1CN(Cc2ccc(Oc3ccccc3)nc2)CCO1]

Example 36 was synthesised in analogy to example 31.
Starting materials: Example 5p (120 mg; 0.60 mmol) and Example 1a (95.5 mg; 0.66 mmol). The mixture was stirred at room temperature during 18 hours. The crude was purified by preparative HPLC. Obtained 140 mg of the desired compound.

Example 36

HPLC-MS; Method: Z011_S03; $R_t$ [min]: 0.88
  MS: 328 [M+H]$^+$
Chiral SFC Method:: I_SA_20_IPA_NH$_3$_001
  $R_t$ [min]: 2.73;
  e.e.:100%
$^1$H NMR (400 MHz, DMSO-d$_6$); δ ppm: 1.90 (m, 1H); 2.11 (m, 1H); 2.57 (m, 3H); 2.61-2.67 (m, 1H); 2.90 (m, 1H); 3.43-3.60 (m, 3H); 3.83-3.89 (m, 2H); 6.99 (d, J=8.37 Hz, 1H); 7.10-7.23 (m, 3H); 7.41 (t, J=7.53 Hz, 2H); 7.62-7.71 (m, 1H); 7.78 (dd, J=8.40, 2.41 Hz, 1H); 8.04 (d, J=2.36 Hz, 1H).

Example 37

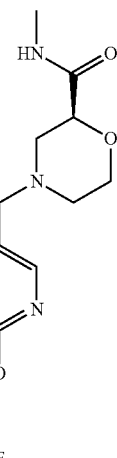

Example 1a (76.9 mg; 0.53 mmol) and example 5q (120 mg; content 95%; 0.49 mmol) were dissolved in THF (3 ml); DIPEA (0.12 ml; 0.68 mmol) was added and the reaction mixture stirred 30 min before the addition of NaBH(OAc)$_3$ (126 mg; 0.60 mmol). The mixture was stirred over 18 hours at room temperature, diluted with MeOH, filtered through a syringe filter and purified by preparative HPLC. The product was diluted with water (5 ml) and the obtained precipitate is filtered off, washed with water and dried in the air. Obtained 106 mg of the desired compound.

Example 37

HPLC-MS; Method: Z011_S03; $R_t$ [min]: 0.93
  MS: 364 (M+H)$^+$
Chiral SFC Method:: I_SA_20_IPA_NH$_3$_001
  $R_t$ [min]: 1.8;
  e.e. 100%
$^1$H NMR (400 MHz, DMSO-d$_6$); δ ppm: 1.91 (m, 1H); 2.05-2.16 (m, 1H); 2.54-2.65 (m, 4H); 2.89 (m, 1H); 3.46-3.59 (m, 3H); 3.82-3.89 (m, 2H); 7.19-7.36 (m, 4H); 7.62-7.69 (m, 1H); 7.85 (m, 1H); 7.99 (m, 1H).

Example 38

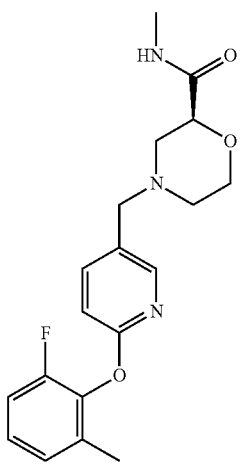 [SMILES: CNC(=O)[C@@H]1CN(Cc2ccc(Oc3c(C)cccc3F)nc2)CCO1]

Example 1a (75.8 mg; 0.53 mmol) and example 5r (130 mg; content 85%; 0.48 mmol) were dissolved in THF (3 ml); DIPEA (0.12 ml; 0.67 mmol) was added and the reaction mixture stirred 30 min before the addition of NaBH(OAc)$_3$ (152 mg; 0.72 mmol). The mixture was stirred over 18 hours at room temperature, diluted with MeOH (3 ml), filtered through a syringe filter and purified by preparative HPLC.

Obtained 129 mg of the desired compound.

Example 38

HPLC-MS; Method: Z003_S05; R$_t$ [min]: 1.10
MS: 360 (M+H)$^+$
Chiral SFC Method:: I_SA_20_IPA_NH$_3$_001
R$_t$ [min]: 1.9;
e.e. 100%
$^1$H NMR (400 MHz, DMSO-d$_6$); δ ppm: 1.89 (m, 1H); 2.05-2.14 (m, 4H); 2.57 (m, 3H); 2.60-2.65 (m, 1H); 2.89 (m, 1H); 3.41-3.59 (m, 3H); 3.82-3.90 (m, 2H); 7.09-7.19 (m, 4H); 7.64-7.70 (m, 1H); 7.80 (m, 1H); 7.96 (m, 1H).

Example 39

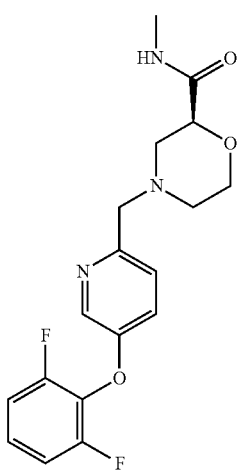 [SMILES: CNC(=O)[C@@H]1CN(Cc2ccc(Oc3c(F)cccc3F)cn2)CCO1]

Example 39 was synthesised in analogy to example 38.

Starting materials: Example 5s (130 mg; content 85%; 0.47 mmol) and Example 1a (74.5 mg; 0.52 mmol). The mixture was stirred at room temperature during 18 hours.

The crude was purified by preparative HPLC. Obtained 75.0 mg of the desired compound.

Example 39

HPLC-MS; Method: Z003_S05; R$_t$ [min]: 1.06
MS: 364 [M+H]$^+$
Chiral SFC Method:: I_SA_20_IPA_NH$_3$_001
R$_t$ [min]: 1.98;
e.e.:100%
$^1$H NMR (400 MHz, DMSO-d$_6$); δ ppm: 1.98 (m, 1H); 2.17 (m, 1H); 2.57 (m, 3H); 2.61-2.69 (m, 1H); 2.93 (m, 1H); 3.54-3.65 (m, 3H); 3.83-3.91 (m, 2H); 7.31-7.45 (m, 5H); 7.67 (m, 1H); 8.32 (m, 1H).

Example 40

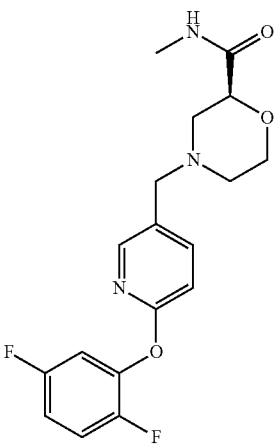 [SMILES: CNC(=O)[C@@H]1CN(Cc2ccc(Oc3cc(F)ccc3F)nc2)CCO1]

Example 40 was synthesised in analogy to example 38.

Starting materials: Example 5t (100 mg; 0.43 mmol) and Example 1a (67.43 mg; 0.47 mmol).

The crude was purified by preparative HPLC. Obtained 130 mg of the desired compound.

Example 40

HPLC-MS; Method: Z003_S05; R$_t$ [min]: 1.08
MS: 364 [M+H]$^+$
Chiral SFC Method:: I_SA_20_IPA_NH$_3$_001
R$_t$ [min]: 1.78;
e.e.:100%

Example 41

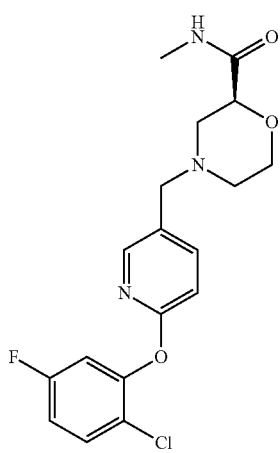 [SMILES: CNC(=O)[C@@H]1CN(Cc2ccc(Oc3cc(F)ccc3Cl)nc2)CCO1]

Example 41 was synthesised in analogy to example 38.
Starting materials: Example 5u (100 mg; 0.4 mmol) and Example 1a (63 mg; 0.44 mmol). Obtained 135 mg of the desired compound.

Example 41

HPLC-MS; Method: Z003_S05; $R_t$ [min]: 1.11
MS: 380 and 382 [M+H]$^+$;
isotopic pattern for 1 Cl observed
Chiral SFC Method:: I_SA_20_IPA_NH$_3$_001
$R_t$ [min]: 2.22; e.e.:100%

What is claimed is:

1. A compound of formula A1 or of formula A2

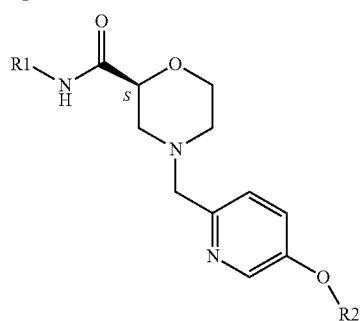
A1

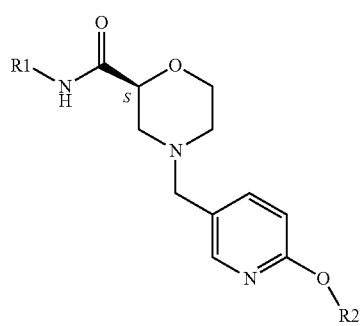
A2 or a pharmaceutically acceptable salt thereof, wherein
R$^1$ is selected from the group consisting of methyl, ethyl, propyl, iso-propyl, cyclopropyl, H$_3$C—CH$_2$—CH$_2$—CH$_2$—, and cyclobutyl; and R$^2$ is phenyl which is optionally substituted with 1, 2 or 3 substituents selected from the group consisting of fluoro, chloro, methyl, ethyl, and cyclopropyl.

2. The compound according to claim 1, or a pharmaceutically acceptable salt thereof wherein
R$^1$ is methyl; and
R$^2$ is selected from the group consisting of:

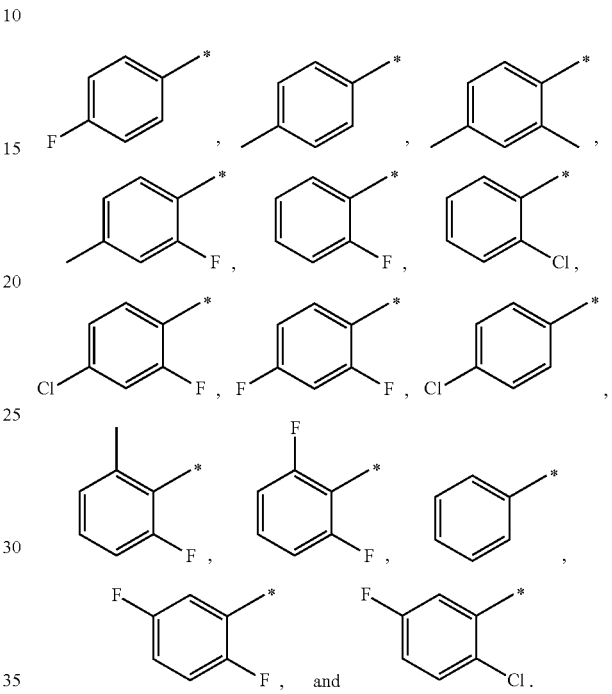

3. The compound according to claim 1, or a pharmaceutically acceptable salt thereof, selected from the group consisting of:

| Ex. | |
|---|---|
| 11 | 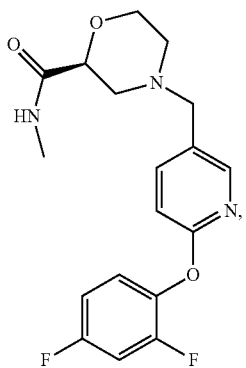 |

-continued
| Ex. | |
|---|---|
| 12 | 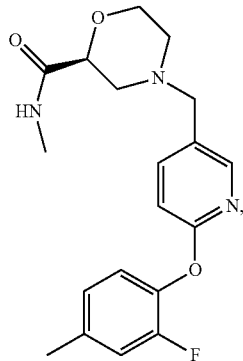 [SMILES: CNC(=O)[C@@H]1CN(Cc2ccc(Oc3ccc(C)cc3F)nc2)CCO1] |
| 13 | 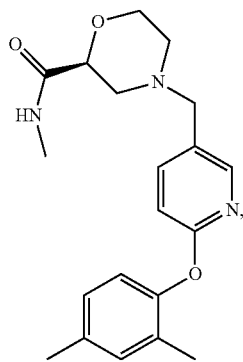 [SMILES: CNC(=O)[C@@H]1CN(Cc2ccc(Oc3ccc(C)cc3C)nc2)CCO1] |
| 14 | 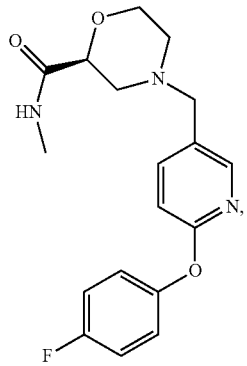 [SMILES: CNC(=O)[C@@H]1CN(Cc2ccc(Oc3ccc(F)cc3)nc2)CCO1] |
| 15 | 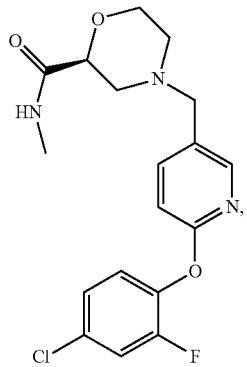 [SMILES: CNC(=O)[C@@H]1CN(Cc2ccc(Oc3ccc(Cl)cc3F)nc2)CCO1] |
-continued
| Ex. | |
|---|---|
| 16 | 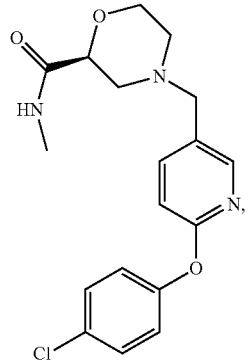 |
| 17 | 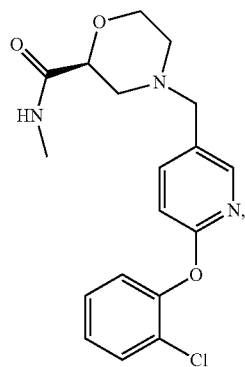 [SMILES: CNC(=O)[C@@H]1CN(Cc2ccc(Oc3ccccc3Cl)nc2)CCO1] |
| 19 | 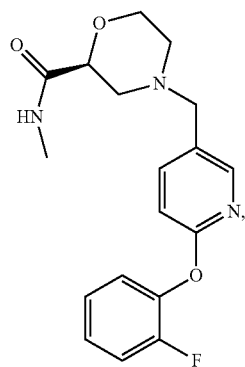 [SMILES: CNC(=O)[C@@H]1CN(Cc2ccc(Oc3ccccc3F)nc2)CCO1] |
| 29 | 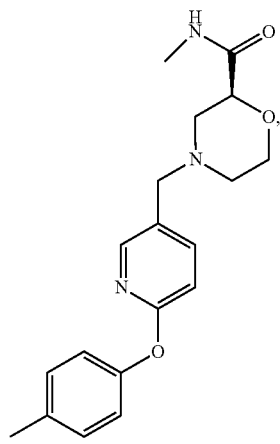 [SMILES: CNC(=O)[C@@H]1CN(Cc2ccc(Oc3ccc(C)cc3)nc2)CCO1] |

| Ex. | |
|---|---|
| 30 | 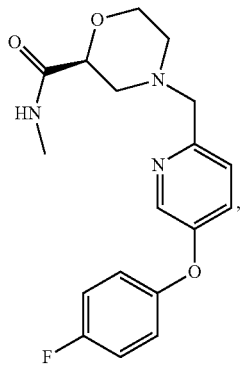 [SMILES: CNC(=O)[C@@H]1CN(Cc2ccc(Oc3ccc(F)cc3)cn2)CCO1] |
| 31 | 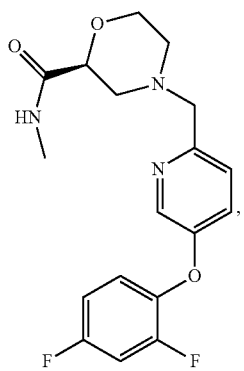 [SMILES: CNC(=O)[C@@H]1CN(Cc2ccc(Oc3ccc(F)cc3F)cn2)CCO1] |
| 32 | 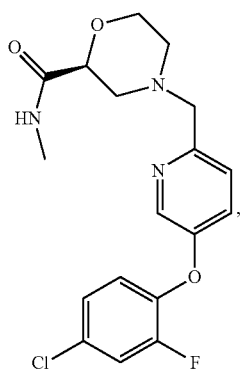 [SMILES: CNC(=O)[C@@H]1CN(Cc2ccc(Oc3ccc(Cl)cc3F)cn2)CCO1] |
| 33 | 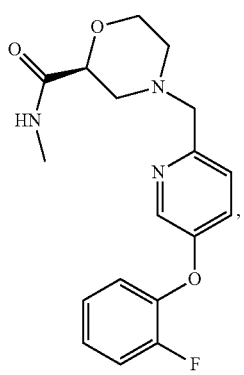 |
| 34 | 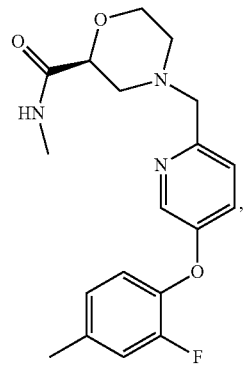 |
| 35 | 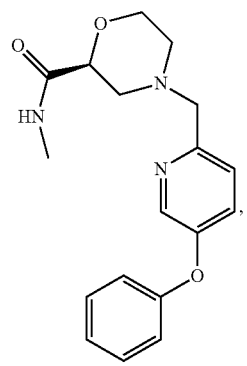 [SMILES: CNC(=O)[C@@H]1CN(Cc2ccc(Oc3ccccc3)cn2)CCO1] |
| 36 | 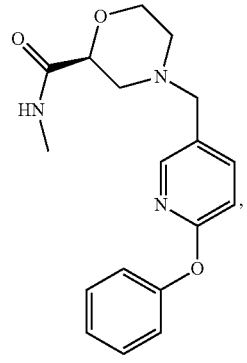 [SMILES: CNC(=O)[C@@H]1CN(Cc2ccc(Oc3ccccc3)nc2)CCO1] |
| 37 | 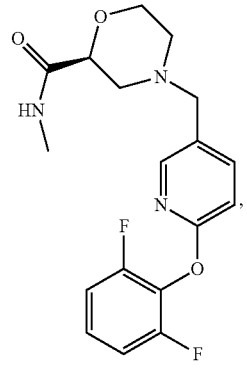 [SMILES: CNC(=O)[C@@H]1CN(Cc2ccc(Oc3c(F)cccc3F)nc2)CCO1] |

| Ex. | |
|---|---|
| 38 | 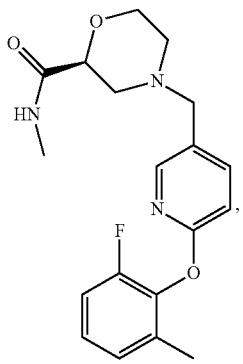 [SMILES: CNC(=O)[C@@H]1CN(Cc2ccc(Oc3c(C)cccc3F)nc2)CCO1] |
| 39 | 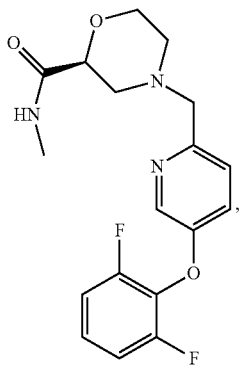 [SMILES: CNC(=O)[C@@H]1CN(Cc2ccc(Oc3c(F)cccc3F)cn2)CCO1] |
| 40 | 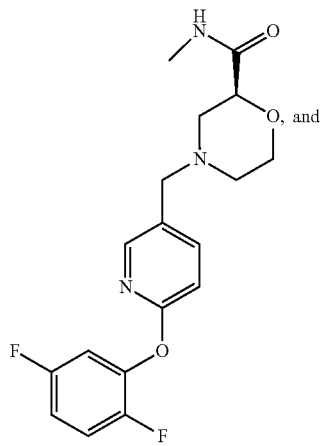 [SMILES: CNC(=O)[C@@H]1CN(Cc2ccc(Oc3cc(F)ccc3F)nc2)CCO1 ; "and"] |

| Ex. | |
|---|---|
| 41 | 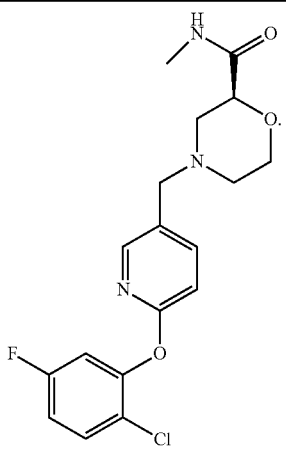 |

4. A pharmaceutically acceptable salt of a compound according to claim 1.

5. A method for treating bipolar disorder I, bipolar disorder II, depression, hypomania, mania or mixed forms thereof, the method comprising administering a pharmaceutically effective amount of a compound of formula A1 or A2 according to claim 1, or a pharmaceutically acceptable salt thereof, to a patient in need thereof.

6. A method for treating single depressive episode or recurrent major depressive disorder, minor depressive disorder, depressive disorder with postpartum onset, or depressive disorders with psychotic symptoms, the method comprising administering a pharmaceutically effective amount of a compound of formula A1 or A2 according to claim 1, or a pharmaceutically acceptable salt thereof, to a patient in need thereof.

7. The method according to claim 5, wherein the compound of formula A1 or A2, or a pharmaceutically acceptable salt thereof, is administered with another antidepressant drug.

8. The method according to claim 5, wherein the patient is further being treated with behavioural therapy.

9. The method according to claim 6, wherein the compound of formula A1 or A2, or a pharmaceutically acceptable salt thereof, is administered with another antidepressant drug.

10. The method according to claim 6, wherein the patient is further being treated with behavioural therapy.

11. A pharmaceutical composition comprising a compound according to claim 1, or a pharmaceutically acceptable salt thereof, in admixture with a pharmaceutically acceptable adjuvant, diluent and/or carrier.

12. The method according to claim 5, wherein the bipolar disorder I or bipolar disorder II includes melancholic features, atypical features, mood-congruent psychotic features, mood-incongruent psychotic features, or mixed features thereof.

* * * * *